(12) United States Patent  
Patton et al.

(10) Patent No.: US 12,397,105 B2
(45) Date of Patent: *Aug. 26, 2025

(54) SYSTEMS AND COMPONENTS FOR REGULATING FLUID INFUSION TO A PATIENT

(71) Applicant: Perceptive Medical Inc., Newport Beach, CA (US)

(72) Inventors: Douglas Patton, Newport Beach, CA (US); Joseph Rinehart, Newport Beach, CA (US); Morgan McKeown, Kailua, HI (US)

(73) Assignee: Perceptive Medical Inc., Newport Beach, CA (US)

( * ) Notice: Subject to any disclaimer, the term of this patent is extended or adjusted under 35 U.S.C. 154(b) by 35 days.

This patent is subject to a terminal disclaimer.

(21) Appl. No.: 18/051,319

(22) Filed: Oct. 31, 2022

(65) Prior Publication Data
US 2023/0087682 A1 Mar. 23, 2023

Related U.S. Application Data

(63) Continuation of application No. 17/529,691, filed on Nov. 18, 2021, now Pat. No. 11,484,645.
(Continued)

(51) Int. Cl.
*A61M 5/145* (2006.01)
*A61M 5/14* (2006.01)
(Continued)

(52) U.S. Cl.
CPC ........ *A61M 5/1452* (2013.01); *A61M 5/1413* (2013.01); *A61M 5/16881* (2013.01);
(Continued)

(58) Field of Classification Search
CPC ............ A61M 5/14228; A61M 5/1413; A61M 2205/12; F04B 3/006; F04B 1/00;
(Continued)

(56) References Cited

U.S. PATENT DOCUMENTS 3,985,133 A 10/1976 Jenkins et al.
4,204,538 A 5/1980 Cannon
(Continued)

FOREIGN PATENT DOCUMENTS

WO 2012097141 A2 7/2012

OTHER PUBLICATIONS

European Patent Office, International Search Report and Written Opinion, Mar. 15, 2022.
(Continued)

*Primary Examiner* — Scott J Medway
*Assistant Examiner* — Anh Bui
(74) *Attorney, Agent, or Firm* — Ryan Dean; Umberg Zipser LLP

(57) ABSTRACT

Various fluid delivery systems are described comprising an infusion pump having a housing with a first opening and a hollow interior portion that is configured to receive a cartridge having a tubing. A pump unit can be disposed within the housing. The pump unit comprises a motor mechanically coupled with a crank shaft or eccentric cam that is configured to move a set of pistons or other objects to thereby compress one or more portions of the tubing over time as the crank shaft or eccentric cam rotates.

16 Claims, 23 Drawing Sheets

Related U.S. Application Data

(60) Provisional application No. 63/115,443, filed on Nov. 18, 2020.

(51) Int. Cl.

| | | |
|---|---|---|
| *A61M 5/168* | (2006.01) | |
| *F04B 1/00* | (2020.01) | |
| *F04B 3/00* | (2006.01) | |
| *F04B 43/02* | (2006.01) | |
| *F04B 43/12* | (2006.01) | |
| *F04B 45/06* | (2006.01) | |

(52) U.S. Cl.
CPC ........... *A61M 5/16886* (2013.01); *F04B 1/00* (2013.01); *F04B 3/006* (2013.01); *F04B 43/025* (2013.01); *F04B 43/12* (2013.01); *F04B 45/062* (2013.01); *A61M 2005/14533* (2013.01); *A61M 2205/12* (2013.01); *A61M 2205/50* (2013.01); *A61M 2205/583* (2013.01)

(58) Field of Classification Search
CPC ........ F04B 1/426; F04B 45/062; F04B 43/12; F04B 43/025; F04B 43/0267
See application file for complete search history.

(56) References Cited

U.S. PATENT DOCUMENTS

| | | | |
|---|---|---|---|
| 4,207,871 A | 6/1980 | Jenkins | |
| 4,314,567 A | 2/1982 | Cannon | |
| 4,404,440 A | 9/1983 | Busche | |
| 4,424,720 A | 1/1984 | Bucchianeri | |
| 4,460,358 A | 7/1984 | Somerville et al. | |
| 4,561,830 A | 12/1985 | Bradley | |
| 4,617,014 A | 10/1986 | Cannon et al. | |
| 4,690,673 A | 9/1987 | Bloomquist | |
| 5,165,874 A * | 11/1992 | Sancoff | A61M 5/14228 417/474 |
| 5,647,854 A | 7/1997 | Olsen et al. | |
| 5,741,121 A | 4/1998 | O'Leary | |
| 5,853,386 A | 12/1998 | Davis et al. | |
| 6,146,109 A | 11/2000 | Davis et al. | |
| 7,648,627 B2 * | 1/2010 | Beden | A61M 1/362223 210/85 |
| 8,118,778 B2 | 2/2012 | Haylor et al. | |
| 11,484,645 B2 * | 11/2022 | Patton | F04B 43/025 |
| 2001/0004444 A1 * | 6/2001 | Haser | A61M 3/0201 417/477.2 |
| 2004/0037723 A1 | 2/2004 | Herwig et al. | |
| 2005/0118048 A1 * | 6/2005 | Traxinger | A61M 1/72 417/477.2 |
| 2009/0043252 A1 | 2/2009 | Haylor et al. | |
| 2011/0313358 A1 | 12/2011 | Hariharesan et al. | |
| 2012/0130309 A1 * | 5/2012 | Hariharesan | A61M 39/281 604/151 |
| 2015/0073338 A1 * | 3/2015 | Waldhoff | A61J 15/0026 604/67 |
| 2015/0182688 A1 | 7/2015 | Dhami | |
| 2021/0369954 A1 * | 12/2021 | Adams | F04B 43/08 |

OTHER PUBLICATIONS

First Office Action for CN Application No. 202111370522.7 dated May 1, 2025, 4 pages (including English Translation).

* cited by examiner

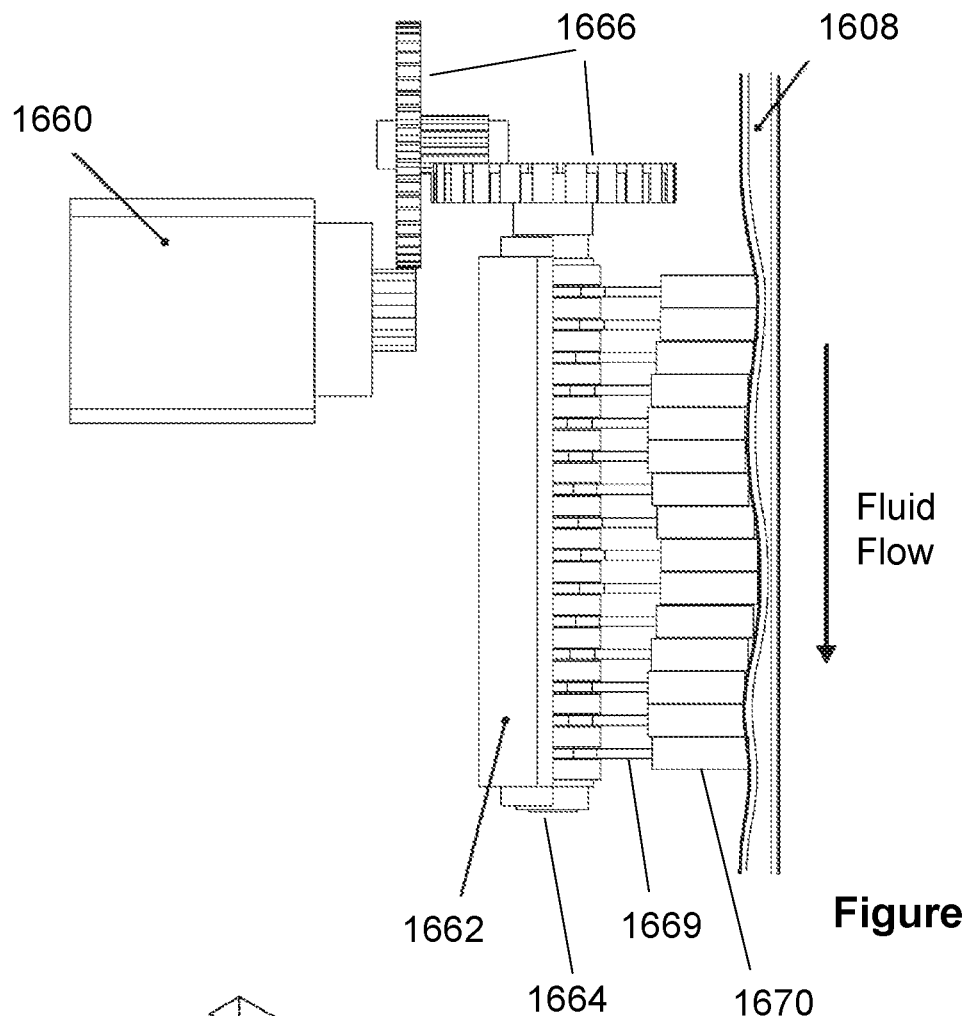
Figure 16C
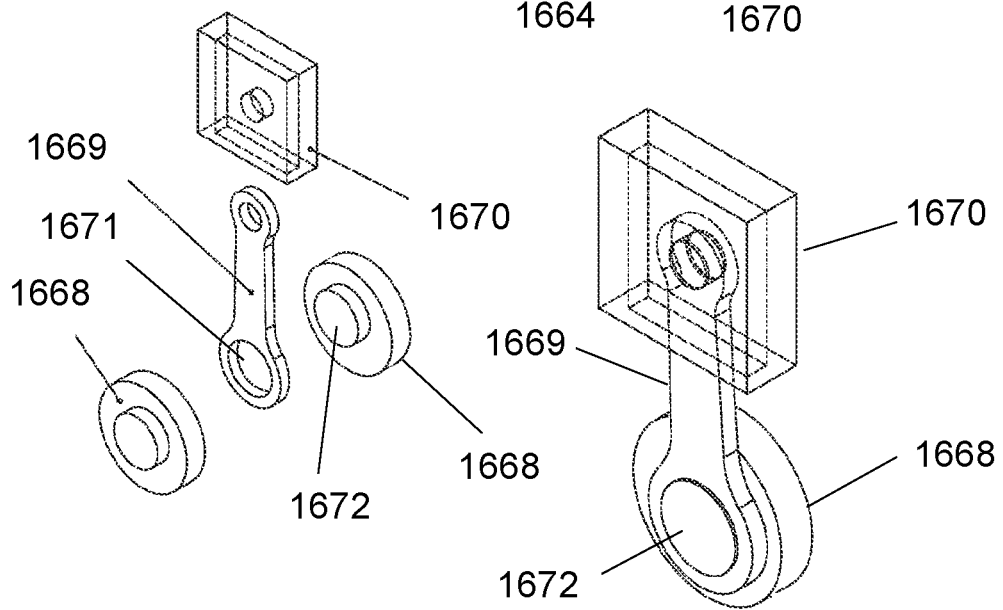
Figure 16D
Figure 16E

SYSTEMS AND COMPONENTS FOR REGULATING FLUID INFUSION TO A PATIENT

This application is a continuation application of U.S. non-provisional patent application having Ser. No. 17/529,691 filed on Nov. 18, 2021, which itself claims priority to U.S. provisional patent application having Ser. No. 63/115,443 filed on Nov. 18, 2020. This and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is fluid infusion devices, and in particular, intravenous fluid infusion pumps.

BACKGROUND

The following description includes information that may be useful in understanding the present invention. It is not an admission that any of the information provided herein is prior art or relevant to the presently claimed invention, or that any publication specifically or implicitly referenced is prior art.

Various pumps exist for fluid infusion to a patient. One of the most common are gravity infusion devices, which utilize gravity to deliver medication. However, such devices are unable to provide precise dosage rates and any information concerning the fluid to be infused.

In an attempt to address these deficiencies, various companies offer volumetric pumps that allow for more precise dosage rates. For example, ALARIS® offers its CAREFUSION® infusion pumps that can provide different dosage rates for multiple medications. Among other problems, such pumps are typically bulky, have a limited user interface, can have the door assembly open unexpectedly resulting in suspension of the medication to the patient, and can be difficult to prime and begin a line of infusion.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there is still a need for improved infusion devices that are easier to use and understand, easier to prime, and provide additional safeguards to prevent unnecessary suspensions and other issues.

SUMMARY OF THE INVENTION

The inventive subject matter provides apparatus, systems and methods for intravenous (IV) infusion devices. Contemplated fluid delivery systems comprise a housing having a first opening leading into a hollow interior portion. Preferably, the first opening and hollow interior portion are configured to receive at least a portion of a cartridge having a tubing.

It is contemplated that the cartridge comprises a housing that is configured to retain a portion of a tubing through which a medication can flow from a medication source to a patient.

A pump unit is disposed within the housing and comprises a motor that is mechanically coupled with an eccentric cam via one or more gears, such that the motor causes rotation of the eccentric cam. Preferably, the eccentric cam is connected or coupled to one or more pistons that are configured to move as the eccentric cam rotates. When the cartridge is disposed within the hollow interior portion, the tubing of the cartridge is disposed adjacent or near the pump unit, such that rotation of the eccentric cam causes the pistons to depress different portions of the tubing over time, and thereby causes flow of a fluid within the tubing at a flow rate that is based on the rotation of the eccentric cam.

Contemplated fluid delivery systems preferably also comprise a display communicatively coupled with the pump unit and configured to display information concerning a patient and a medication delivery, for example. Preferably, the display is a touch-screen display or otherwise configured to allow input of commands from a medical professional. For example, using the display, it is contemplated that a dosage of medication being delivered to a patient can be varied by the medical professional.

Preferably, the display is physically separate from the housing and communicatively coupled with the pump unit via a wired or wireless connection. In such embodiments, it is preferred that the display can be attached or otherwise coupled to an IV pole and disposed to be approximately at an eye height level of a user. To allow for proper ergonomics, it is contemplated that the display could be vertically moved up and down the IV pole until a desired height is reached. The display could also be rotated about the IV pole. In some contemplated embodiments, the display could be tilted up and/or down to facilitate viewing of the information on the display.

In some embodiments, the tubing may enter a top portion of the cartridge housing and exit through a bottom portion of the cartridge housing. It is preferred, though not necessary, that the tubing enters and exits through a front surface or face of the cartridge housing (e.g., the surface facing away from the interior portion of the cartridge). In some embodiments, a portion of the tubing that extends generally horizontally through the cartridge can be disposed at an angle greater than zero degrees from a horizontal surface, meaning that the tubing moves lower with respect to the cartridge housing as the tubing moves from the face to the back of the housing. This can be helpful to cause any air bubbles within the tubing to flow upwardly (e.g., toward the face of the housing) and out of the cartridge.

The cartridge preferably comprises an actuator coupled to a valve that inhibits a flow of fluid in the tubing. The valve is configured to compress the tubing to prevent fluid flow in the tubing of the cartridge when the valve is in a first position. This advantageously prevents unintentional flow of fluid through the cartridge. Preferably, the valve is biased in the first position such as by using a spring to thereby prevent the flow of fluid when the actuator is not engaged.

When the actuator is depressed or otherwise engaged, the valve is moved to a second position that allows fluid to flow through the tubing of the cartridge. Preferably, the actuator is disposed on, and extends outwardly from, an outer surface of the cartridge housing. In some embodiments, the actuator may be at least slightly tapered, such that insertion of the cartridge within an intravenous (IV) delivery system will depress the actuator when the cartridge is inserted into the delivery system.

It is contemplated that the infusion pump could comprise one or more sensors to provide various information to the infusion pump, display, control unit, or other device. As one example, the pump unit or other component of the device could comprise one or more sensors which are configured to monitor a flow rate of the fluid within the tubing of the cartridge. As another example, the pump unit could comprise one or more sensors configured to sense or determine properties of the fluid within the tubing, such as a concentration or type of medication or other fluid within the tubing. Such sensors could include, for example, chemical sensors, optical sensors, resistance sensors, and so forth.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 16C illustrates an enlarged portion of the infusion pump of FIG. 16B.

FIG. 16D illustrates an exploded view of one embodiment of a piston and tie rod for a pump unit.

FIG. 16E illustrates an assembled view of the piston and tie rod of FIG. 16D.

DETAILED DESCRIPTION

Throughout the following discussion, numerous references may be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

Figure 1A:
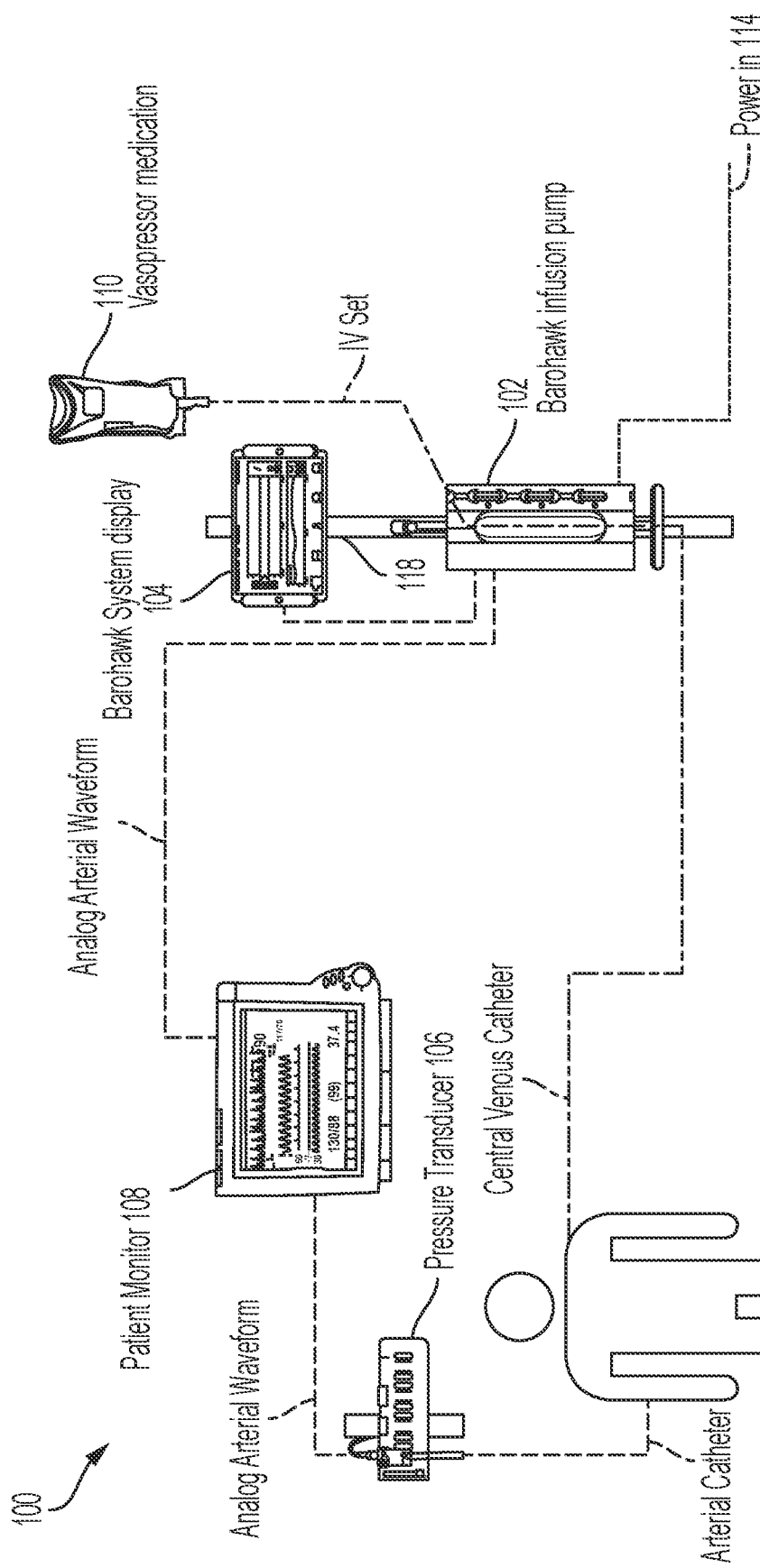
FIG. 1A illustrates a flowchart of one embodiment of a fluid delivery system.

FIG. 1A illustrates a flowchart of one embodiment of a fluid delivery system 100. System 100 preferably comprises an infusion pump 102 communicatively coupled with a display 104, which is preferably separable from the pump 102. The infusion pump 102 preferably receives information about one or more vital signs of a patient 112 from one or more sensors 106. Such information can be received directly from the one or more sensors 106 or via an intermediary device such as a patient monitor 108, for example.

The infusion pump 102 preferably regulates a flow of medication 110 or other fluid through the pump 102 and thereby controls the flow rate of the fluid and thus a delivery of the medication 110 or other fluid to the patient 112. The pump 102 preferably receives power from a line voltage 114; however, it is contemplated that the pump 102 could have a battery backup to continue to regulate fluid flow if power to the infusion pump 102 is shut off or temporarily disconnected.

In some embodiments, both the display 104 and the infusion pump 102 could be mounted to or otherwise coupled to a pole 118.

Figure 1B:
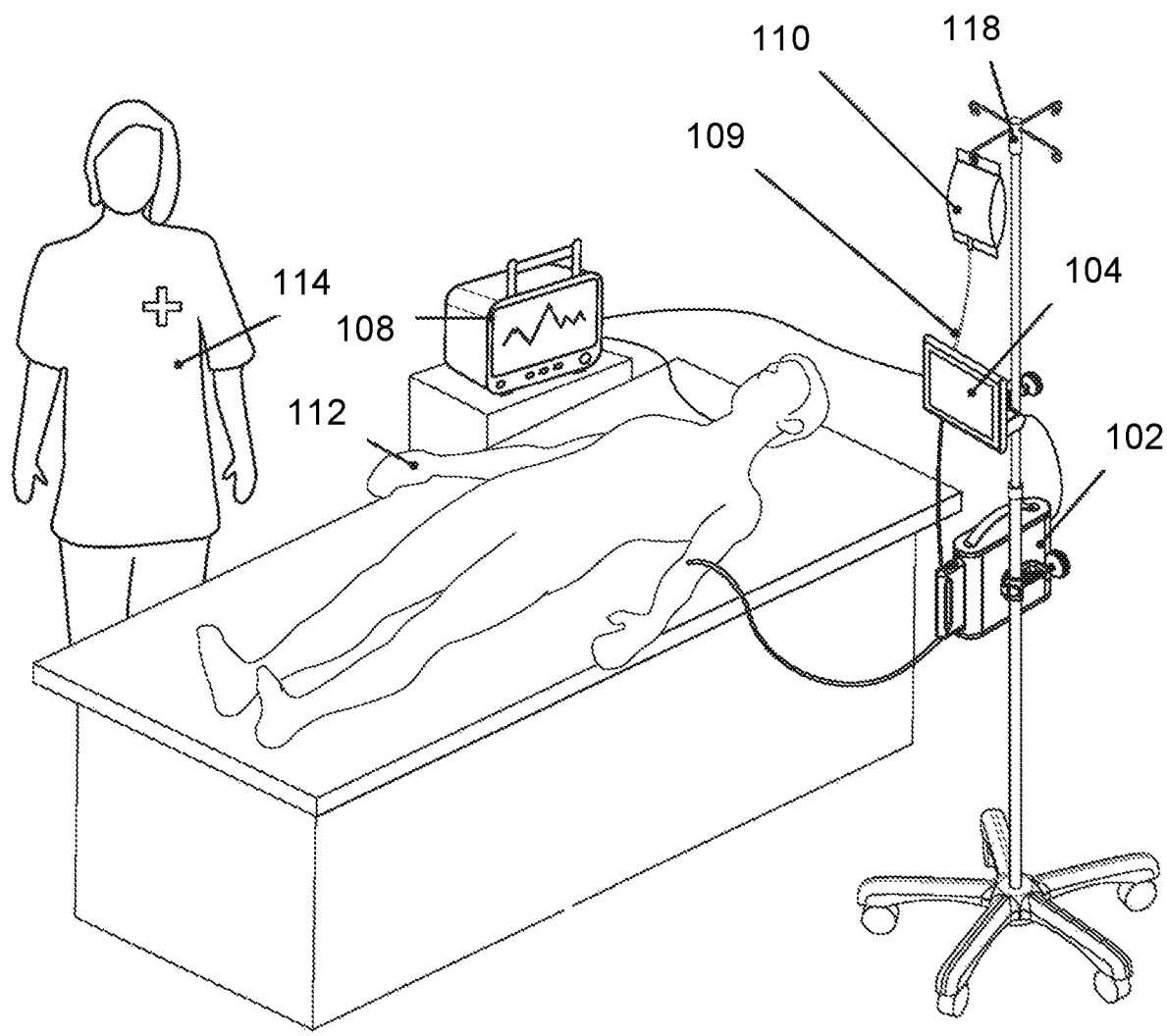
FIG. 1B illustrates one embodiment of a fluid delivery system.

FIG. 1B illustrates one embodiment of a fluid delivery system, which comprises an infusion pump 102 communicatively coupled with a display 104. Preferably, the display 104 is separable from the pump 102. The infusion pump 102 preferably receives information about one or more vital signs of a patient 112 from one or more sensors, which could be monitored by a patient monitor 108 or another intermediary device. In other embodiments, the sensors could transmit information directly to the infusion pump 102. Contemplated sensors could include, for example, a pressure transducer, a thermometer, a heart rate monitor, a blood oxygen monitor, and so forth. Using the display, for example, a medical professional 114 could input commands or review information about the patient 112 and/or medication delivery.

The infusion pump 102 preferably regulates a flow of medication 110 or other fluid from a source such as an IV bag through the infusion pump 102 and to the patient 112. Preferably, the infusion pump 102 controls a flow rate of the medication 110 or other fluid through the tubing 109 and thus controls an amount of the medication 110 or other fluid being delivered to the patient 112 over a specific period of time. In some embodiments, both the display 104 and the infusion pump 102 could be mounted to or otherwise coupled to a pole 118.

Figure 2:
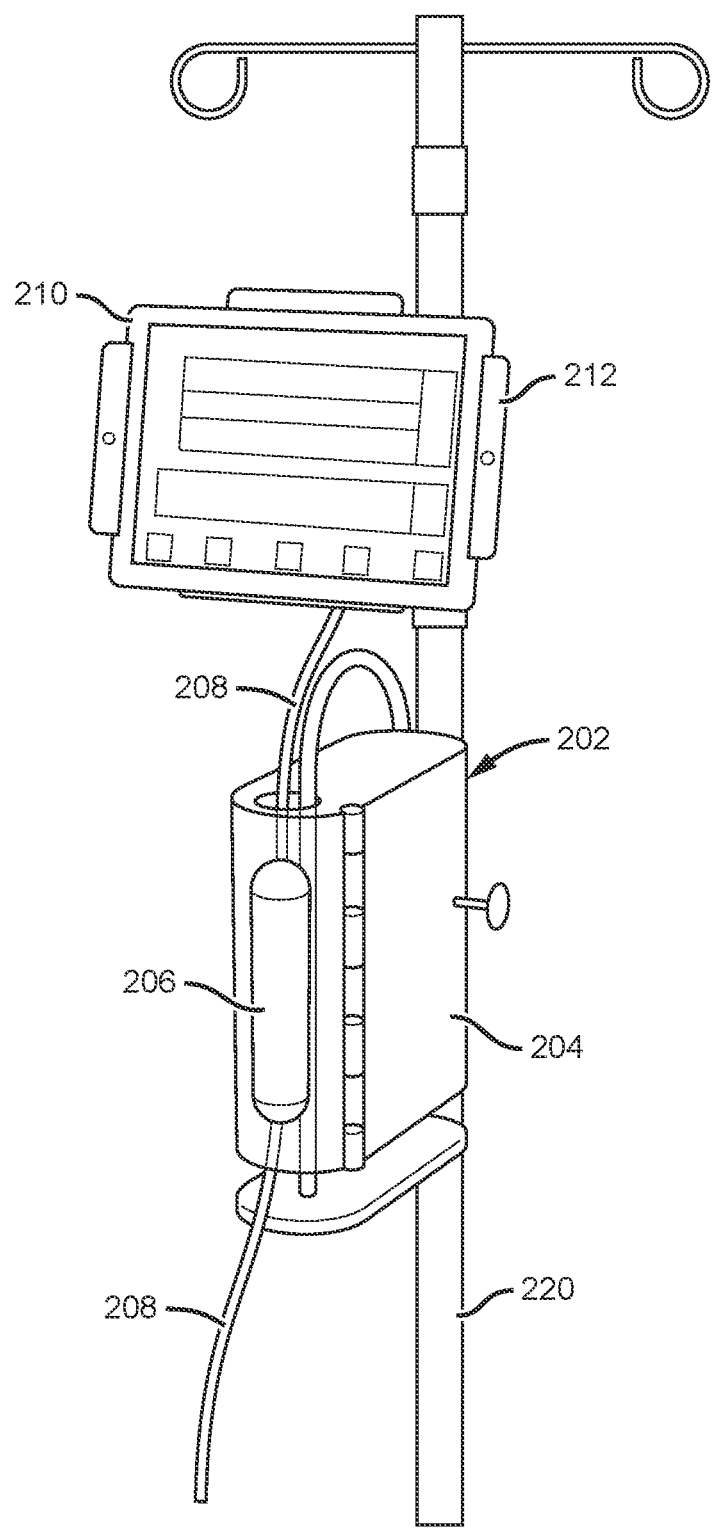
FIG. 2 illustrates one embodiment of an infusion pump and display.

FIG. 2 illustrates one embodiment of an infusion pump 202 comprising a housing 204 configured to receive a cartridge 206 having a tubing 208. The infusion pump 202 preferably comprises a controller having a processor and memory, wherein the memory is configured to store one or more control algorithms. The controller is configured to control a motor of the pump unit which thereby regulates a flow of the fluid within the tubing 208 of the cartridge 206. In some embodiments, the controller can be configured to also control a latching mechanism such as one or more solenoids to release the cartridge 206.

A display 210 is communicatively coupled with the infusion pump 202 and configured to display information concerning a flow of medication to the patient as well as information concerning one or more vital signs of the patient. Preferably, the display 210 comprises a display screen which may be a touch screen or other technology that allows for inputting of one or more commands via touching or otherwise interacting with the display 210. Of course, it is contemplated that commands could be inputted via other methods such as by voice, a keyboard, a mouse, or other input device. In this manner, it is contemplated that a command can be received at the display 210 and then transmitted from the display 210 to the infusion pump 202.

Preferably, each of the display 210 and the infusion pump 202 can be separable and mechanically coupled to a pole 220, such that both the display 210 and the infusion pump 202 can be mounted to the pole 220. Preferred mounting apparatus allows for the display 210 and the infusion pump 202 to move vertically along the pole 220 to thereby adjust a height of each relative to the floor other surface. In some embodiments, the mounting apparatus of the display 210 can also allow for angular adjustment such that the display 210 can be rotated and/or tilted with respect to the pole 220.

In some embodiments, the display 210 can be held in place via a dock 212, which is mechanically coupled to the pole 220. In this manner, the display 210 can be removably coupled to the dock 212, such that the display 210 can be removed from the dock 212 and be held by a medical professional or other user, for example. It is contemplated that the dock 212 may comprise one or more connections that provide for power and a wired data connection to the display 210 when the display 210 is inserted into the dock 212.

Figure 3:
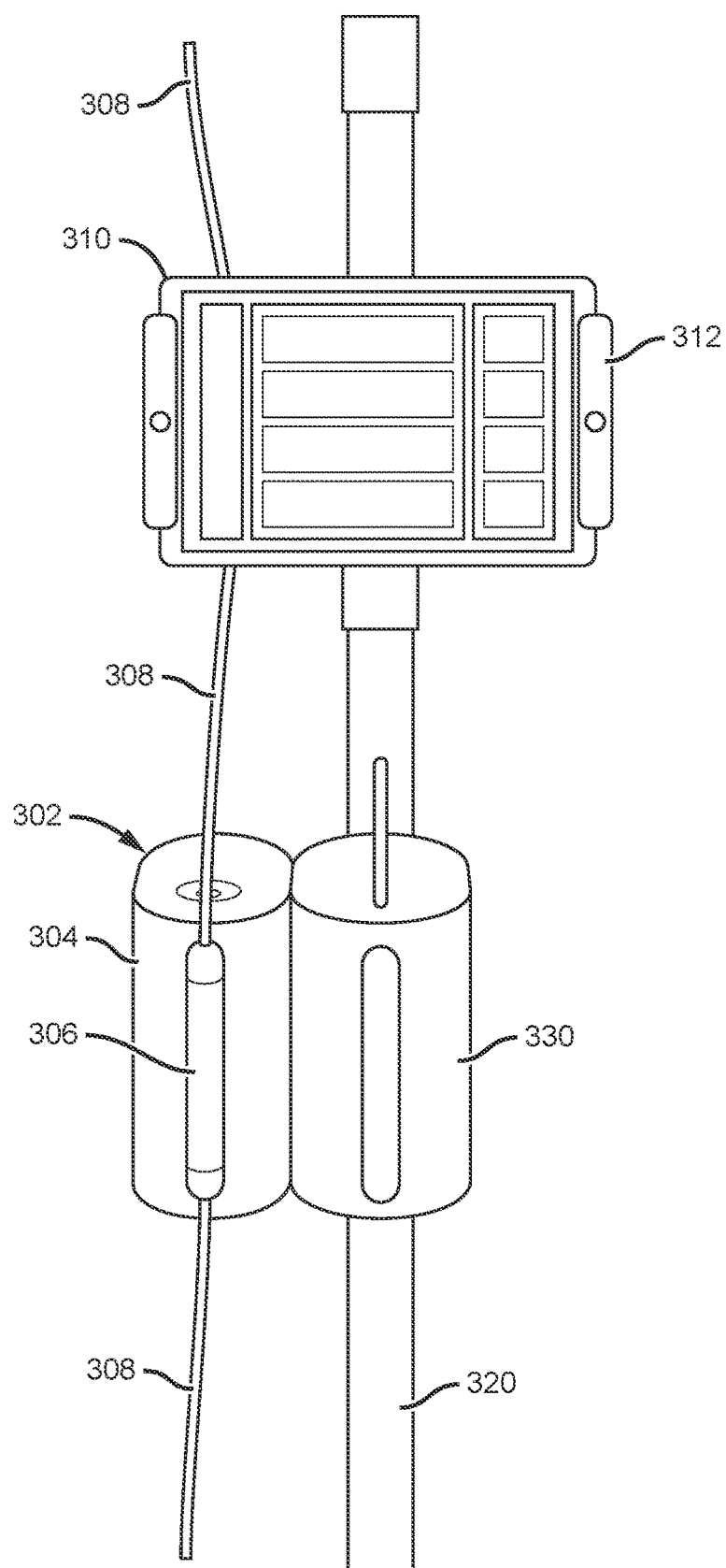
FIG. 3 illustrates another embodiment of an infusion pump and display.

Rather than include a control unit (controller) in the housing of the infusion pump 202, it is alternatively contemplated that the infusion pump 302 can be communicatively coupled with a control unit 330 disposed outside of the housing, such as shown in FIG. 3. Similar to that discussed above, the control unit 330 preferably comprises a processor and memory, wherein the memory is configured to store one or more control algorithms. The control unit 330 is communicatively coupled with the infusion pump 302 (directly or indirectly via a wired or wireless connection) to control the infusion pump 302, and in some embodiments, the control unit 330 may control multiple infusion pumps with each infusion pump regulating a flow of a different medication of fluid.

The control unit 330 is configured to control a pump unit and/or motor of the infusion pump 302 which thereby regulates a flow of fluid within a tubing 308 of the cartridge 306 disposed within the pump 302. In some embodiments, the control unit 330 can be configured to control a latching mechanism such as one or more solenoids to release the cartridge upon command of the controller. A more detailed discussion of exemplary latching mechanisms is provided below. With respect to the remaining numerals in FIG. 3, the same considerations for like components with like numerals of FIG. 2 apply.

Figure 4:
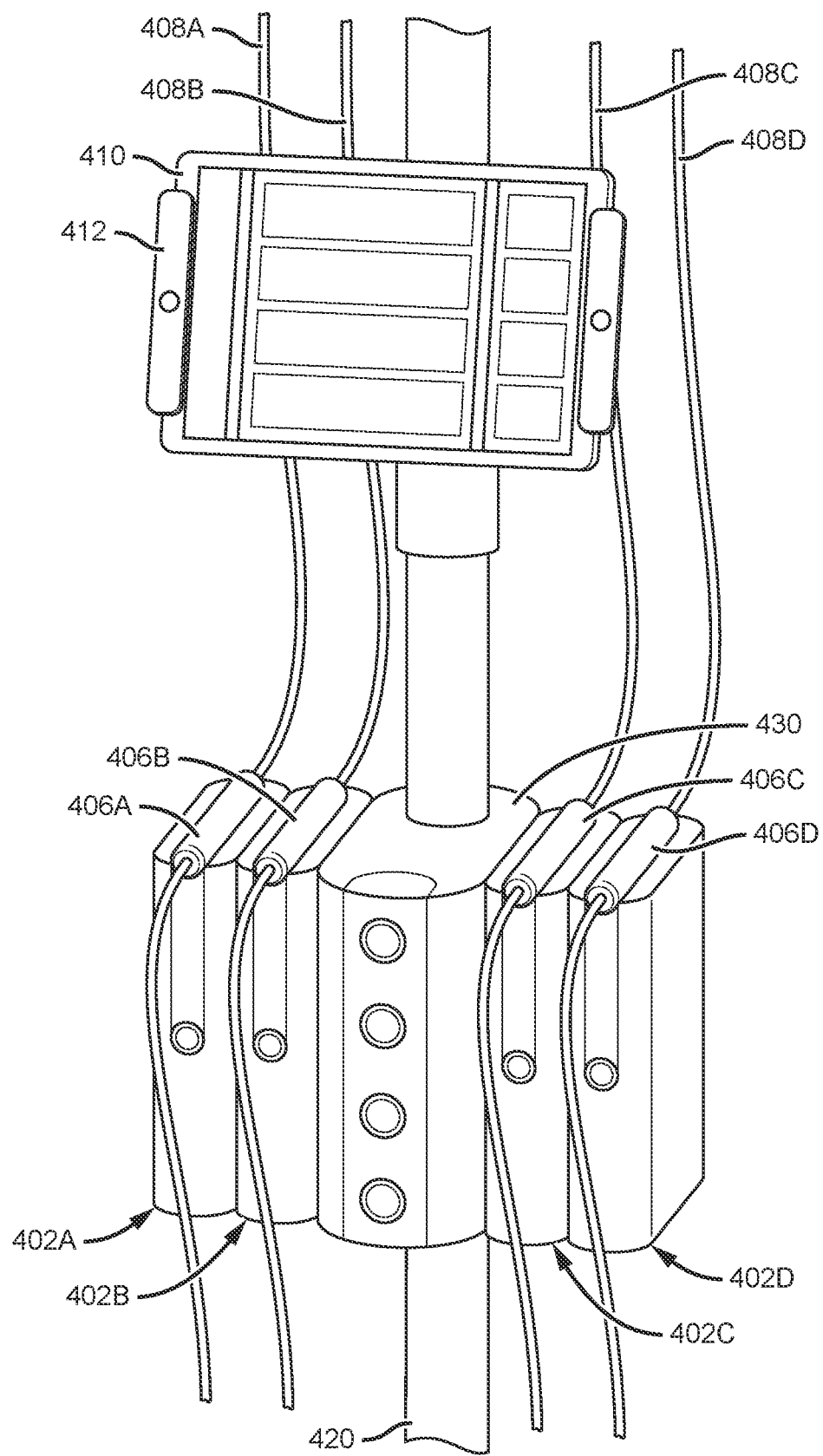
FIG. 4 illustrates another embodiment of an infusion pump and display.

FIG. 4 illustrates a control unit 430 communicatively coupled to four infusion pumps 402A-402D. Similar to that discussed above, the control unit 430 comprises a processor and memory, wherein the memory is configured to store one or more control algorithms. The control unit 430 is configured to control each of the infusion pumps 402A-402D, and specifically, a motor of each of the infusion pumps 402A-402D to regulate a flow of fluid within a tubing 408A-408D of a cartridge 406A-406D inserted within each of the infusion pumps 402A-402D, respectively. In some embodiments, the control unit 430 can be configured to also control a latching mechanism such as one or more solenoids to release the cartridge 406A, 406B, 406C or 406D disposed within one of the infusion pumps 402A-402D.

The control units described herein with respect to the various embodiments and whether disposed within or outside of the infusion pump can be configured to receive signals and/or information and transmit command signals. For example, a control unit can be configured to receive signals and/or information concerning one or more vital signs of a patient, and based on the information received, change a dosage rate of medication to the patient. This can occur, for example, by the control unit causing the motor in a pump unit to increase or decrease the RPMs, such as by varying a voltage to the motor, based on one or more algorithms stored in a memory of the control unit and/or one or more variables, limits or factors.

In contrast to the infusion pump shown in FIG. 2 in which the pump has an opening on the front-facing surface to receive a cartridge, the infusion pumps 402A-402D each has an opening on a top surface of the infusion pump that is configured to receive a cartridge 406A-406D, respectively. With respect to the remaining numerals in FIG. 4, the same considerations for like components with like numerals of FIG. 2 apply.

Figure 5:
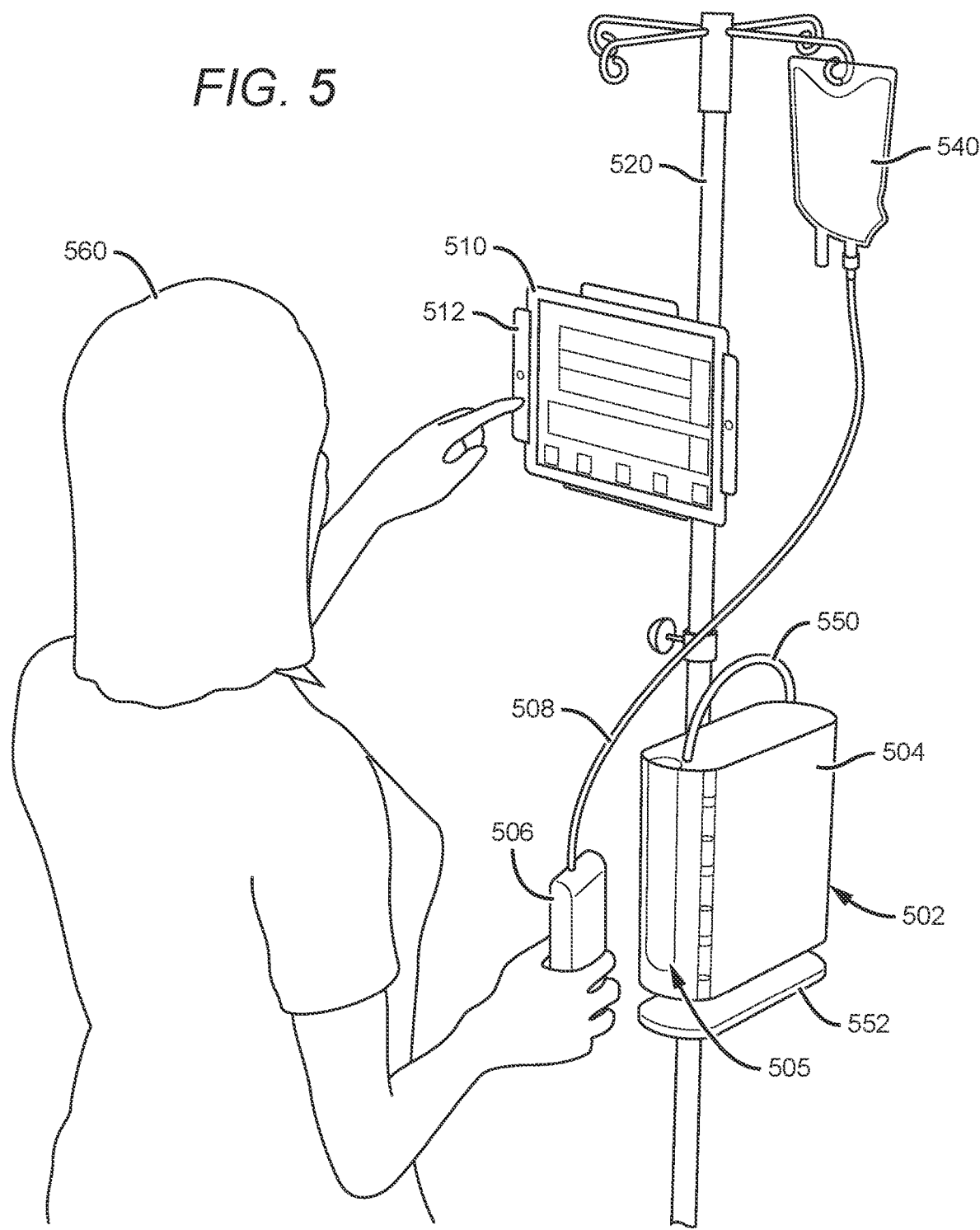
FIG. 5 illustrates another embodiment of an infusion pump and display.

FIG. 5 illustrates another embodiment of an infusion pump 502 comprising a housing 504 having a first opening 505 and a hollow interior portion. Preferably, a cartridge 506 can be inserted into the first opening 505 and at least partially within the hollow interior portion. Cartridge 506 preferably comprises a portion of a tubing 508, which can be connected at one end to a fluid source 540 and at the other end to a patient. When the cartridge 506 is inserted within the housing 504, the cartridge is preferably retained within the housing 504 using one or more latch mechanisms, such as described below.

The infusion pump 502 can optionally include a handle 550 to facilitate carrying of the infusion pump 502. In some embodiments, a power cable for the infusion pump 502 can be wrapped about the handle 550 when the cable is not in use. In other embodiments, the cable can be wrapped about a foot 552 of the infusion pump 502 when not in use.

Display 510 can be communicatively coupled with the infusion pump 502 via a wired or wireless connection and configured to display information concerning a flow of medication to a patient as well as information concerning one or more vital signs of the patient on a display screen of the display 510. Preferably, display 510 has a touch screen or other technology that allows for inputting of one or more commands via touching or otherwise interacting with the display 510. In this manner, it is contemplated that a command can be received at the display 510 and then transmitted from the display 510 to the infusion pump 502. In the embodiment shown in FIG. 5, it is contemplated that the infusion pump 502 comprises a control unit disposed within the housing 504 and configured to control a pump unit that is also disposed in the housing 504. Exemplary pump units are described in more detail below.

Preferably, each of the display 510 and the infusion pump 502 can be separable from one another and mechanically coupled to a pole 520, such that both the display 510 and the infusion pump 502 can be mounted or otherwise coupled to the pole 520. Preferred mounting apparatus allows for the display 510 and the infusion pump 502 to move vertically along the pole 520. In some embodiments, the mounting apparatus of the display 510 can allow for angular adjustment such that the display 510 can be tilted and/or rotated with respect to the pole 520. In such embodiments, the display 510 and infusion pump 502 can thereby be adjusted to a desired height for a medical professional 560.

In some embodiments, the display 510 can be held in place via a dock 512, which is mechanically coupled to the pole 520. In this manner, the display 510 can be removably coupled to the dock 512, such that the display 510 can be removed and hand-held by a user, for example.

Additionally or alternatively, it is contemplated that the display 510 could be hingedly coupled to the infusion pump 502 such that the display 510 could be rotated and/or tilted with respect to the infusion pump 502. In alternative embodiments, it is contemplated that the infusion pump 502 could have a slot or other mechanism to receive a portion of the display 510 such that the display 510 can be secured to the pump 502 during transport, for example.

With respect to the remaining numerals in FIG. 5, the same considerations for like components with like numerals of FIG. 2 apply.

FIGS. 6A-6D illustrate one embodiment of a latching mechanism 640 comprising a latching solenoid that is configured to engage an aperture or notch/recess/indentation 607 of the cartridge 606 having a tubing 608 when the cartridge 606 is properly situated within the housing 604 of the infusion pump 602. Preferably, the latching mechanism 640 is a pull solenoid that is biased in a first position shown in FIGS. 6A-6B, in which a projection of the latching mechanism 640 is disposed within the aperture or notch/recess/indentation 607 of the cartridge 606. It is preferred that the cartridge 606 has a curved or tapered upper surface and, optionally a curved or tapered bottom surface, such that the latching mechanism 640 is depressed as the cartridge 606 is inserted and until the latching mechanism 640 is displaced into the aperture or notch/recess/indentation 607 of an outer surface of the cartridge 606.

Figure 6A:
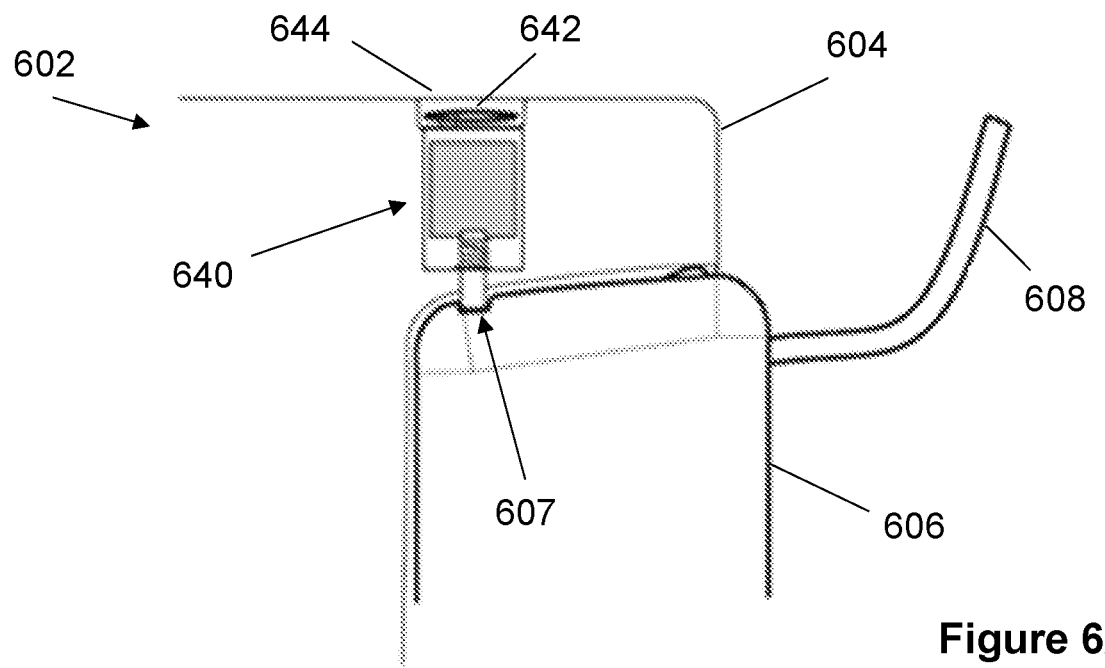
FIGS. 6A-6D illustrate one embodiment of a latching mechanism for an infusion pump.
Figure 6B:
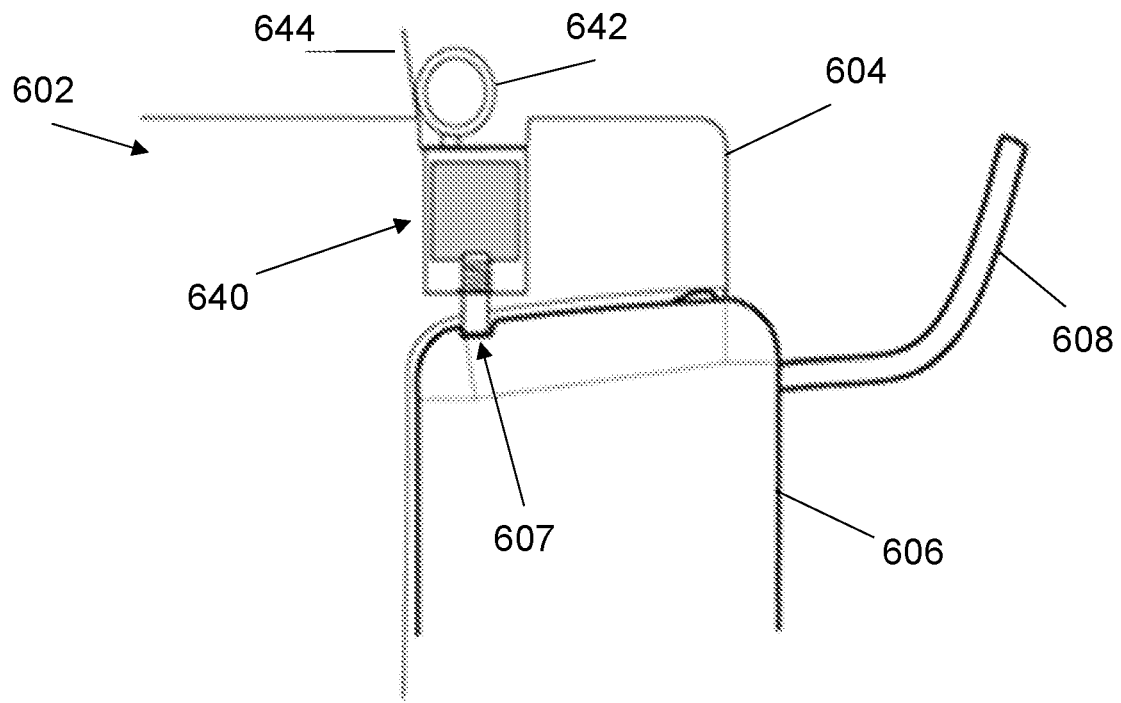
Figure 6C:
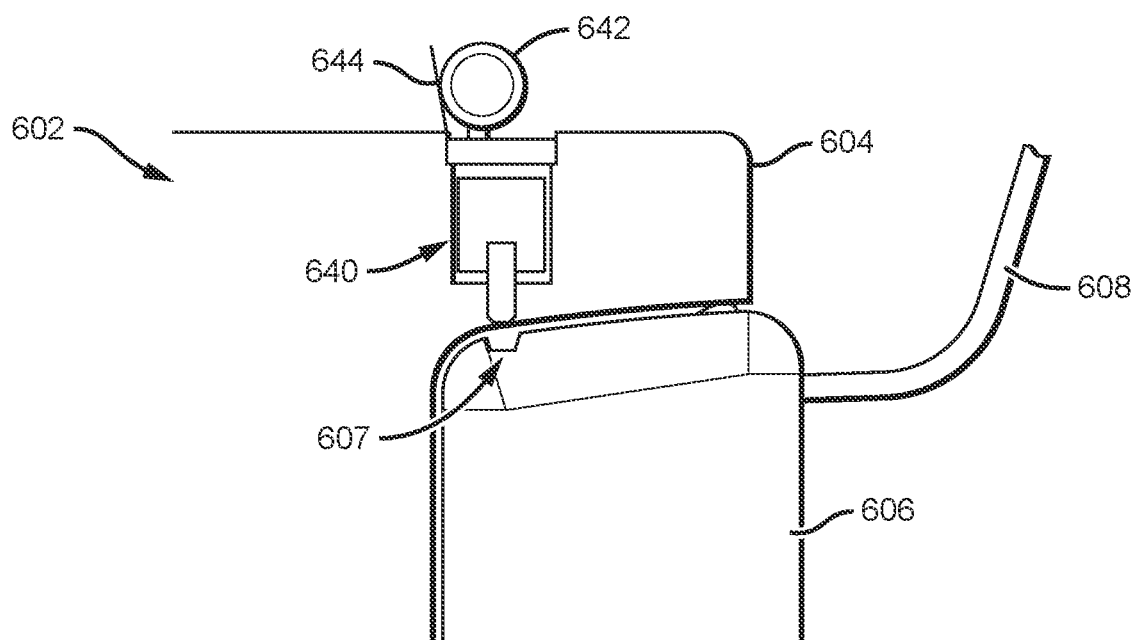
Figure 6D:
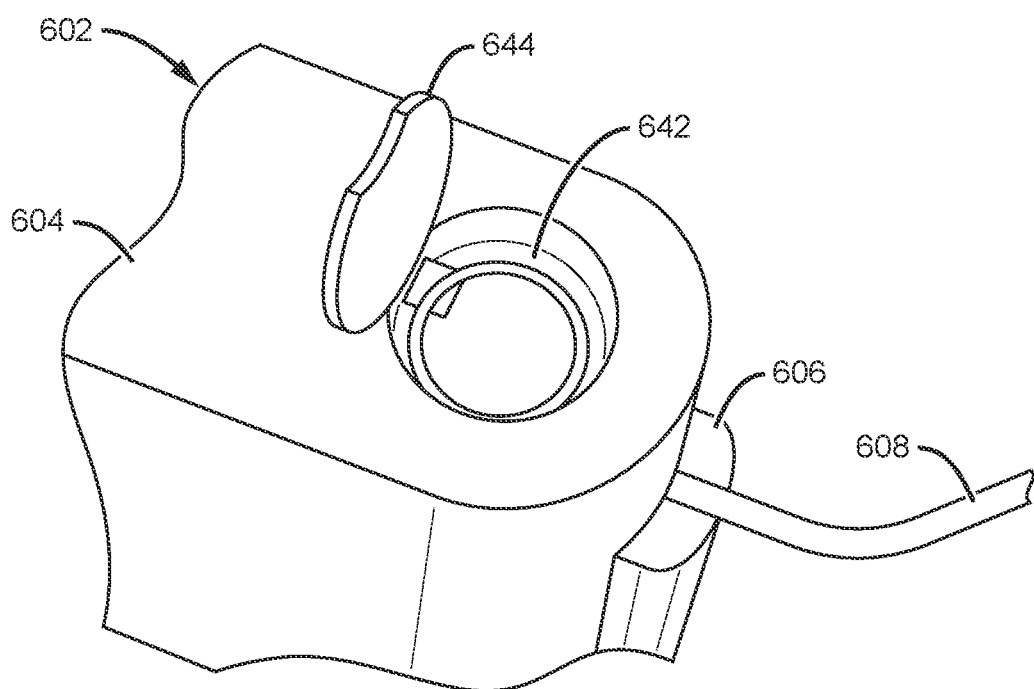

As shown in FIGS. 6A-6D, the latching mechanism 640 can be mechanically coupled to an emergency release 642 that can be hidden by a cover 644 on an outer surface of the housing 604 when not in use. The emergency release 642 can advantageously be used to change a position of the latching mechanism 640 to the position shown in FIG. 6C, and thereby release the cartridge 606 when the latching mechanism 640 is not functioning such as due to a power outage or failure of the latching mechanism 640. In some embodiments, the emergency release 642 comprises a metal part with a snap ring that when pulled releases the engagement of the latching mechanism 640 with the cartridge 606, such as shown in FIG. 6C.

Figure 7A:
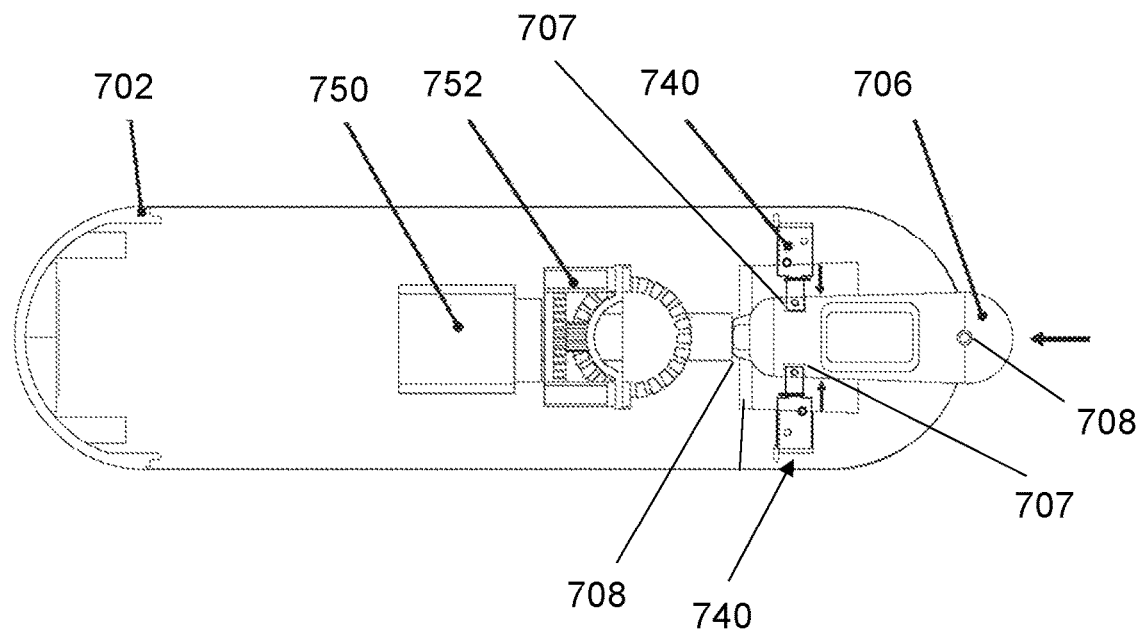
FIGS. 7A-7B illustrate another embodiment of a latching mechanism for an infusion pump.
Figure 7B:
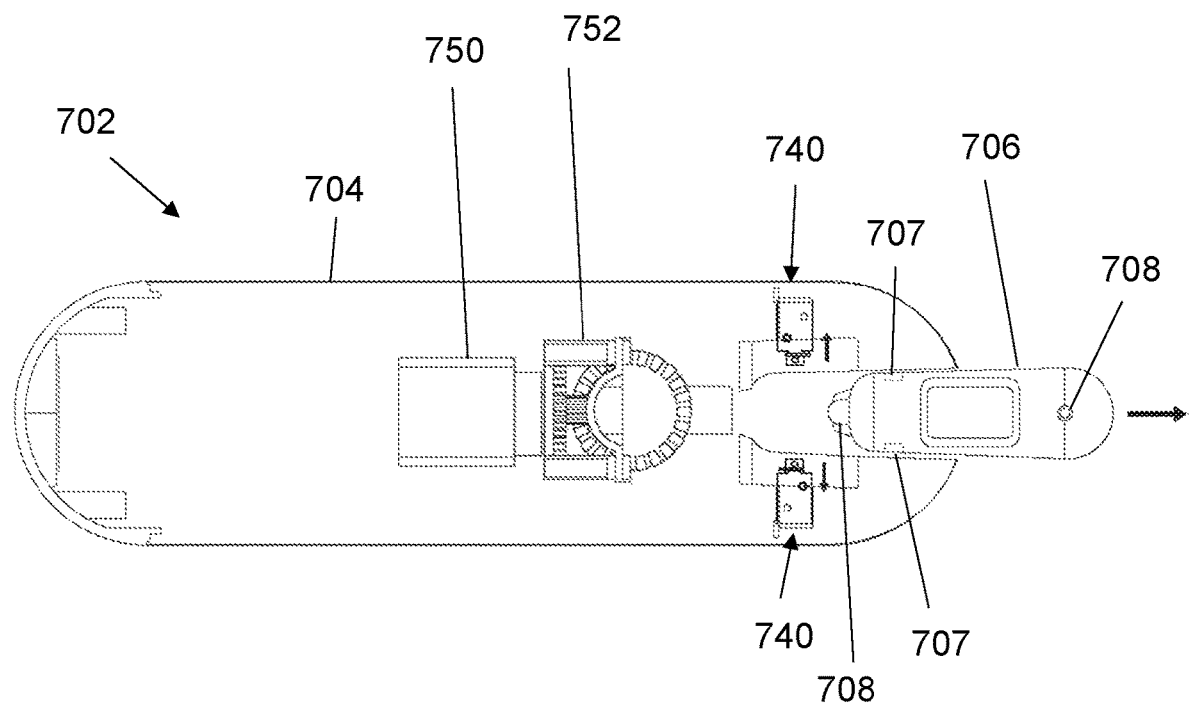

FIGS. 7A-7B illustrate another embodiment of infusion pump 702 having a housing 704 into which a cartridge 706 may be inserted. As discussed above, the pump 702 can include a motor 750 that is connected to and drives a pump assembly 752, which is used to cause and regulate a flow of fluid within a tubing 708 of the cartridge 706.

The infusion pump 702 may comprise one or more latching mechanisms 740 configured to keep the cartridge 706 from inadvertently being removed from the pump 702. Preferred latching mechanisms 740 comprise a latching solenoid that is configured to engage a recess or notch 707 of the cartridge 706 when the cartridge 706 is properly disposed within the housing 704 of the infusion pump 702. Preferably, the latching mechanism 740 is a pull solenoid that is biased in a first position (shown in FIG. 7A) where a projection of the latching mechanism 740 engages notch 707 in the sidewall of the cartridge 706. As shown in FIG. 7A-7B, preferably the housing 704 of the infusion pump 702 comprises two latching mechanisms 740 disposed on left and right sides of the housing 704. In this manner, when the cartridge 706 is properly inserted within the housing 704, the latching mechanisms 740 each engage a recess or notch 707 on the left and right sides of the cartridge 706.

As discussed above in relation to the latching mechanism of FIGS. 6A-6D, it is contemplated that latching mechanisms 740 could each have an emergency release such as that described above to ensure the cartridge 706 can be manually released from the housing 704 if needed.

Figure 8:
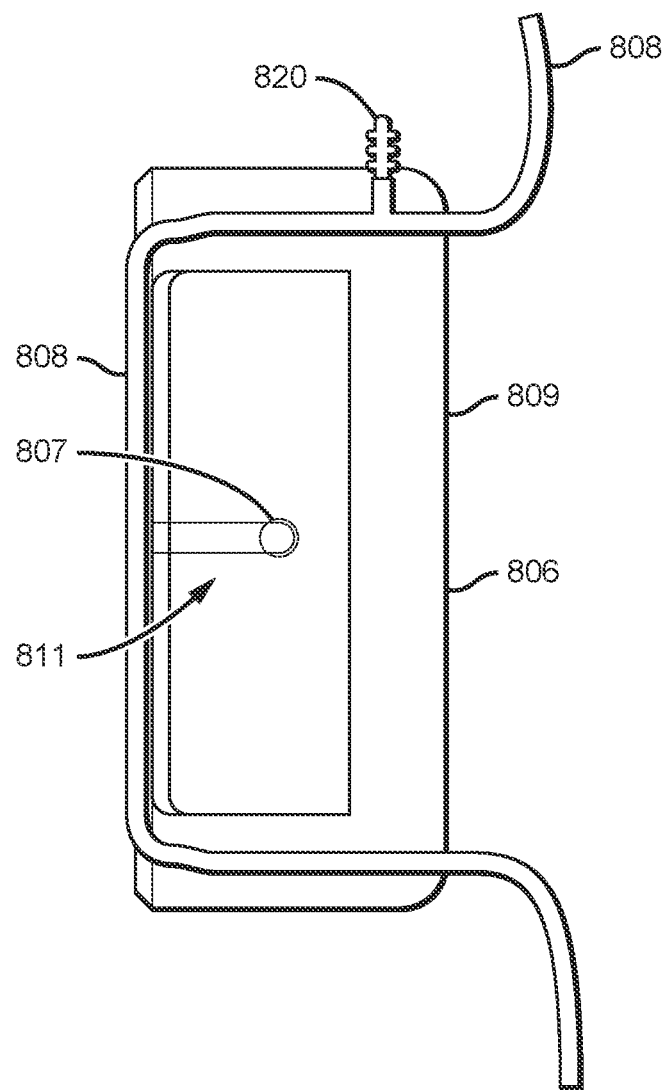
FIG. 8 illustrates one embodiment of a cartridge for an infusion pump.

FIG. 8 illustrates one embodiment of a cartridge 806 having a cartridge housing 809 and a tubing 808, with a portion of the tubing 808 extending through the cartridge 806 to create a C-shape. As shown, cartridge housing 809 can comprise notches or recessed areas 807 on left and right sides of the cartridge housing 809 that are each configured to receive a portion of a latching mechanism, such as those described herein.

In some embodiments, the left and right sides of the cartridge housing 809 may comprise a recessed area 811 that leads to the notch or recessed area 807, which thereby keeps the latching mechanism disengaged until the latching mechanism is at the notch or recessed area 807.

As shown in FIG. 8, the tubing is preferably held flat at the back of the cartridge 806, such that when the cartridge 806 is properly inserted within the housing of the infusion device, the tubing at the back of the cartridge 806 is pressed against a pump unit. Tubing 808 preferably enters and exits through a front surface of the cartridge 806 and loops about to form a C-shape.

Cartridge 806 further comprises a valve 820 that facilitates priming of the cartridge 806. The valve 820 can comprise a bleed valve, which can be actuated using a push button or pull tab, for example. When the valve 820 is in a first position, the tubing 808 can be compressed to thereby prevent fluid from flowing through the tubing. When the valve 820 is in a second position, the tubing 808 is decompressed such that fluid can flow through the tubing 808, such as to prime the tubing.

It some embodiments, the cartridge housing 809 is preferably transparent or translucent, to allow for light to be emitted through the cartridge 806.

Figure 9A:
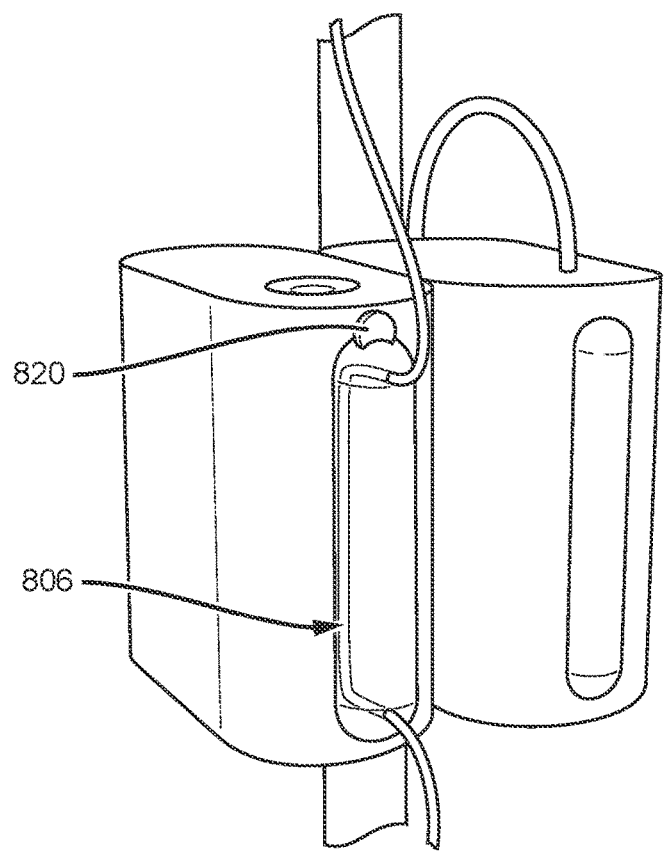
FIG. 9A illustrates the cartridge of FIG. 8 with the bleed valve is a closed position.
Figure 9B:
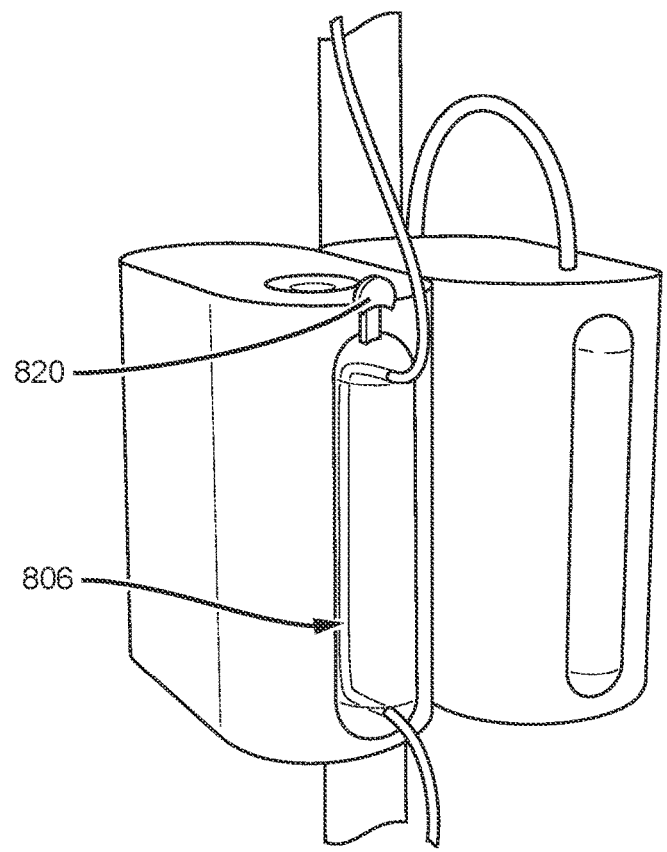
FIG. 9B illustrates the cartridge of FIG. 8 with the bleed valve is an open position.

FIG. 9A illustrates cartridge 806 in which the valve 820 is in the first position (tubing compressed). FIG. 9B illustrates the cartridge 806 in which the valve 820 is in the second position (tubing decompressed).

In an alternative embodiment, an actuator coupled to a valve could be used, where the actuator comprises a push button to cause the valve to move from a first position (closed) to a second position (open) when the actuator is depressed. It is contemplated that the valve could comprise a hook that is disposed about the tubing such as described below and shown in FIGS. 16F-16G. The valve could have a spring that causes the valve to be biased in the first position where the hook compresses the tubing and prevents fluid flow through the tubing. When the actuator is pressed, the hook can move away from the tubing allow fluid to flow through the tubing. Preferably, the push button actuator is disposed on, and extends outwardly away from, an outer surface of the cartridge housing, such as the top surface. Because the cartridge is sized to be held in one hand, the user can prime the cartridge by depressing the push button actuator with a finger of the hand holding the cartridge. In such embodiments, it is contemplated that the push button actuator can be depressed when the cartridge is inserted within the housing of the infusion pump such that fluid can flow through the tubing.

Figure 10:
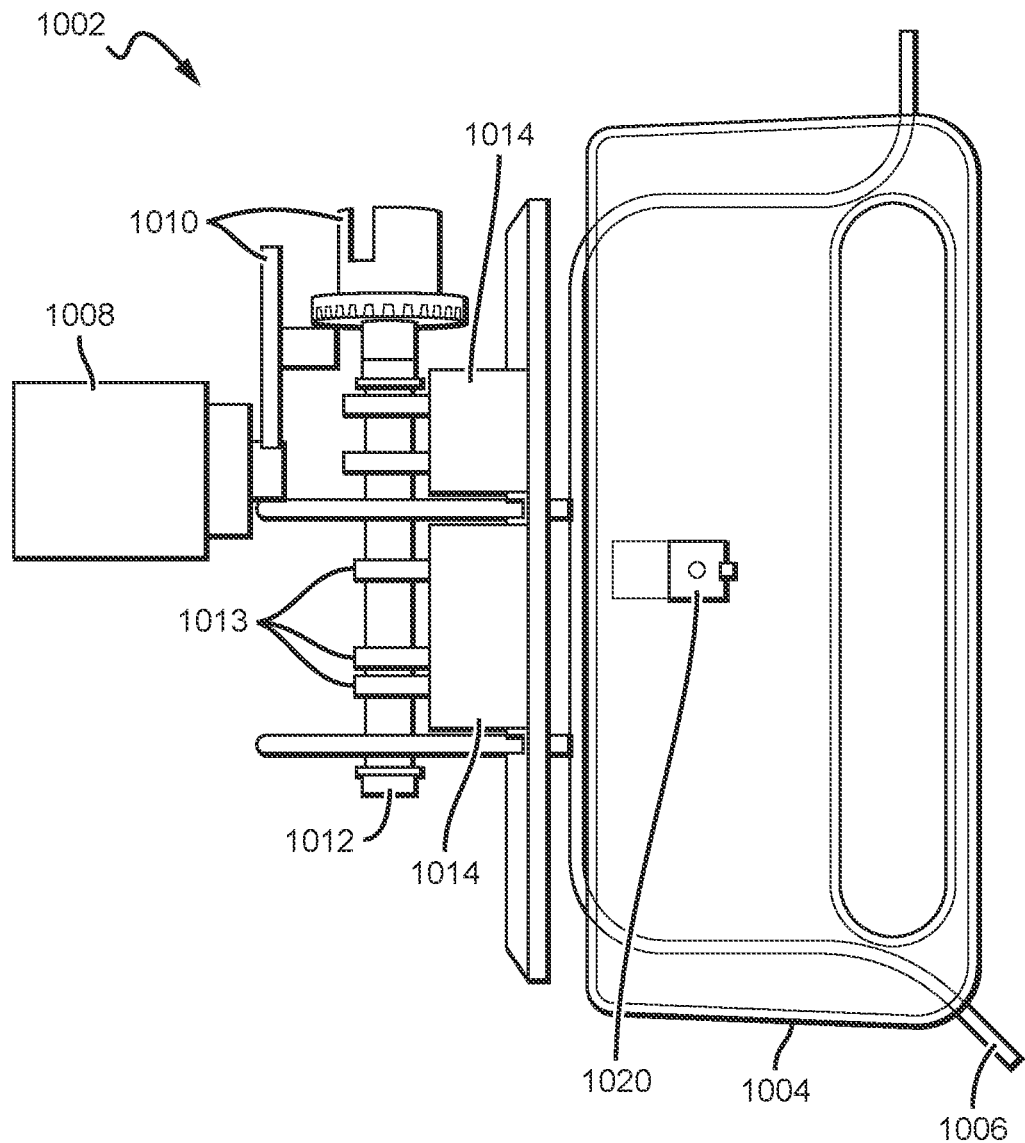
FIG. 10 illustrates another embodiment of a fluid delivery system.

FIG. 10 illustrates a fluid delivery system 1000 of an infusion pump that comprises a pump unit 1002 disposed within the housing of an infusion pump. Preferably the infusion pump is configured to receive a cartridge 1004 having a tubing 1006 that extends through the cartridge 1004 to form a C-shape, for example. When the cartridge 1004 is inserted into the housing of the infusion pump, the tubing 1006 at the back of the cartridge 1004 is pressed against a portion of the pump unit 1002.

As shown, the pump unit 1002 comprises a variable-speed motor 1008 mechanically coupled to an eccentric cam 1012 via a set of gears 1010. In this manner, motor 1008 causes rotation of the cam 1012. Preferably, the cam 1012 comprises a single injection molded piece to reduce overall wear of the cam 1012 over time. The cam 1012 preferably comprises a plurality of circular disks or sheaves 1013 disposed on an axle of the cam 1012, with at least some of the disks or sheaves 1013 being disposed on the axle such that a center of the disk or sheave 1013 is offset from a center of the axle of the cam 1012. It is contemplated that the cam 1012 could be modular and replaceable, which allows the pump unit 1002 to be easily serviced over the lifespan of the pump unit 1002.

The cam 1012 is preferably adjacent to one or more pads 1014, which are pressed sequentially against the tubing 1006 as the cam 1012 rotates and the sheaves 1013 contact the pads 1014. As the pads 1014 are pressed against the tubing 1006 and then released, this causes fluid to flow within the tubing 1006. The more often the pads 1014 press against the tubing 1006 and then are released within a predetermined period of time, the greater the flow rate of the fluid through the tubing.

The fluid delivery system 1000 preferably comprises latching mechanisms 1020, which retain the cartridge 1004 within the housing of the infusion pump when engaged with the cartridge 1004. Preferably, the latching mechanisms 1020 comprise pull solenoids that engage with a notch or recessed area on left and right sides of the cartridge 1004, such as described above.

In some embodiments, cartridge 1004 comprises left and right indentations to facilitate a user's grip on the cartridge 1004.

Figure 11:
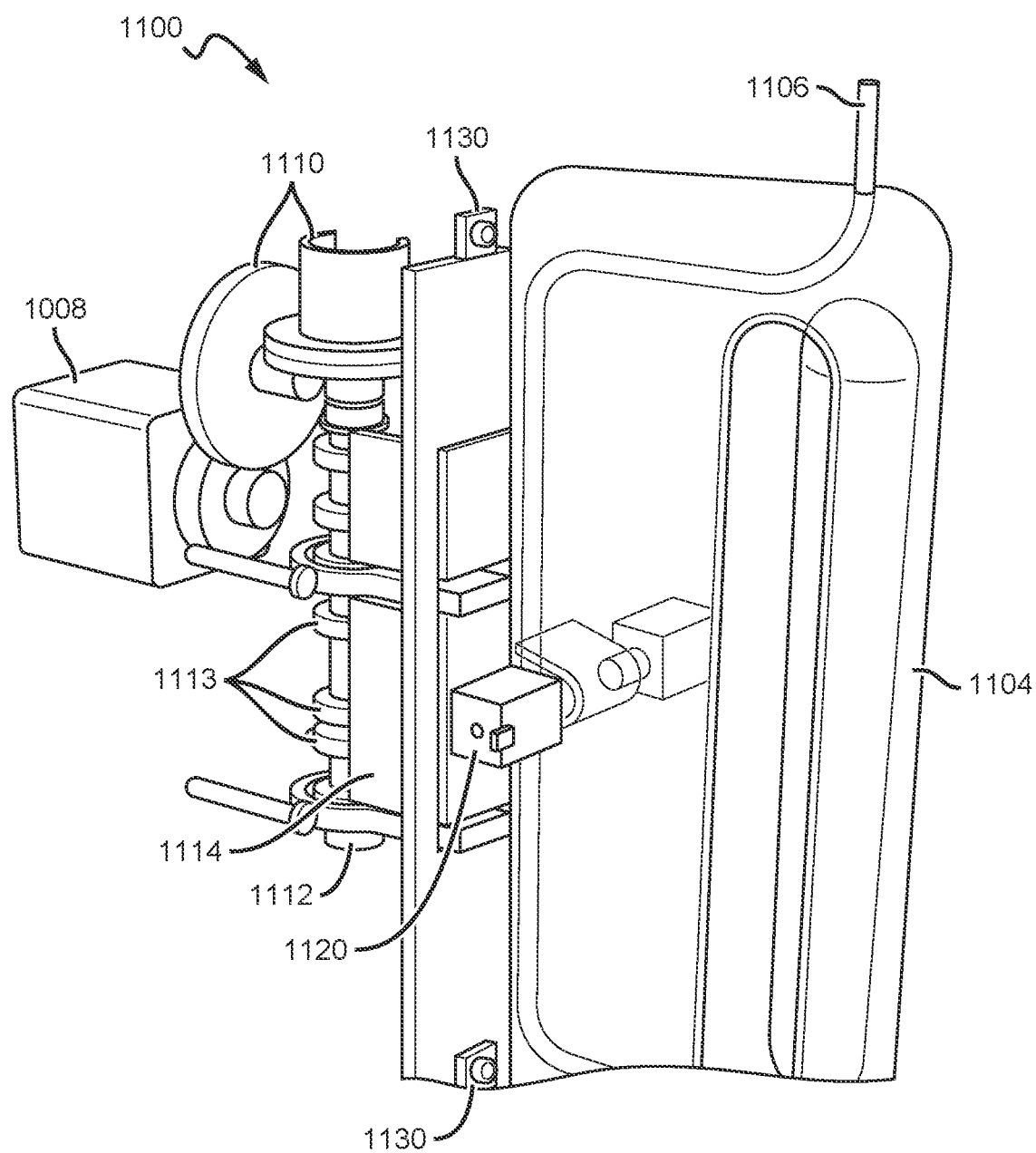
FIG. 11 illustrates another embodiment of a fluid delivery system.

FIG. 11 illustrates another embodiment of a fluid delivery system 1100 of an infusion pump having light sources 1130 that can be used to illuminate the cartridge 1104, for example. In this manner, it is contemplated that the light sources 1130 can be used to visually indicate, for example, a status of the fluid delivery system 1100, when an alert is generated, when an alarm is generated, when the system requires attention, and so forth.

Figure 12A:
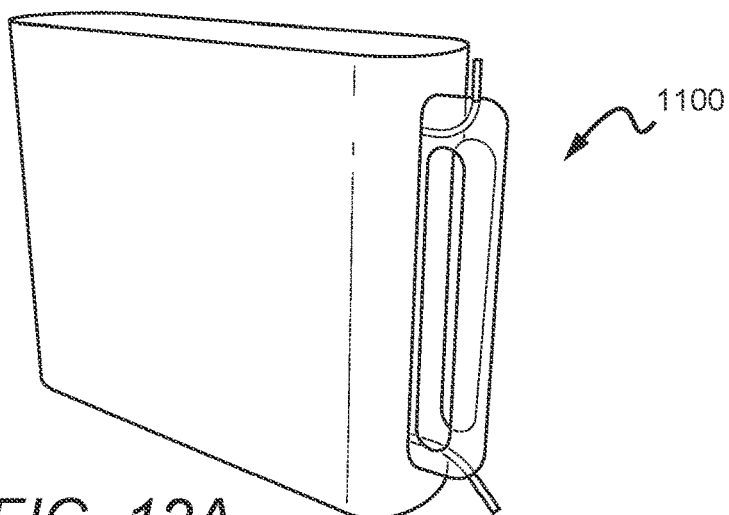
FIGS. 12A-12C illustrate the fluid delivery system of FIG. 11 illuminated in green, yellow and red, respectively.
Figure 12B:
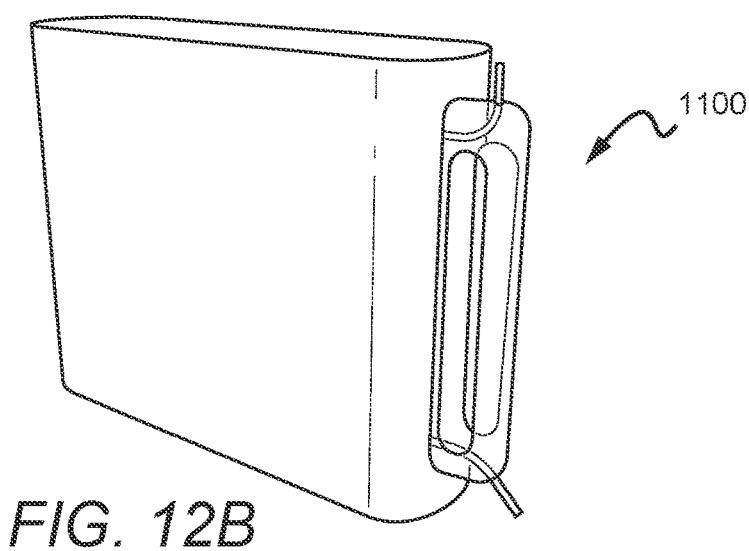
Figure 12C:
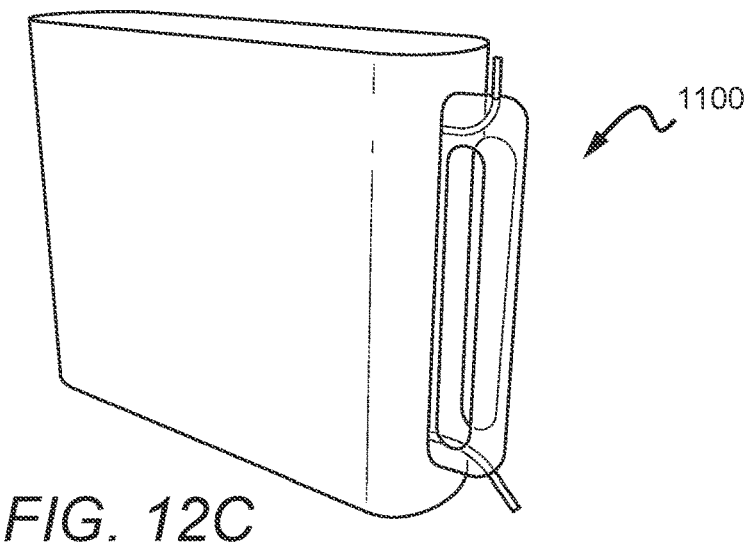

FIGS. 12A-12C illustrate the cartridge being illuminated by light sources within the fluid delivery system 1100, with FIG. 12A showing the cartridge being illuminated green, FIG. 12B showing the cartridge being illuminated yellow, and FIG. 12C showing the cartridge being illuminated red.

Figure 13A:
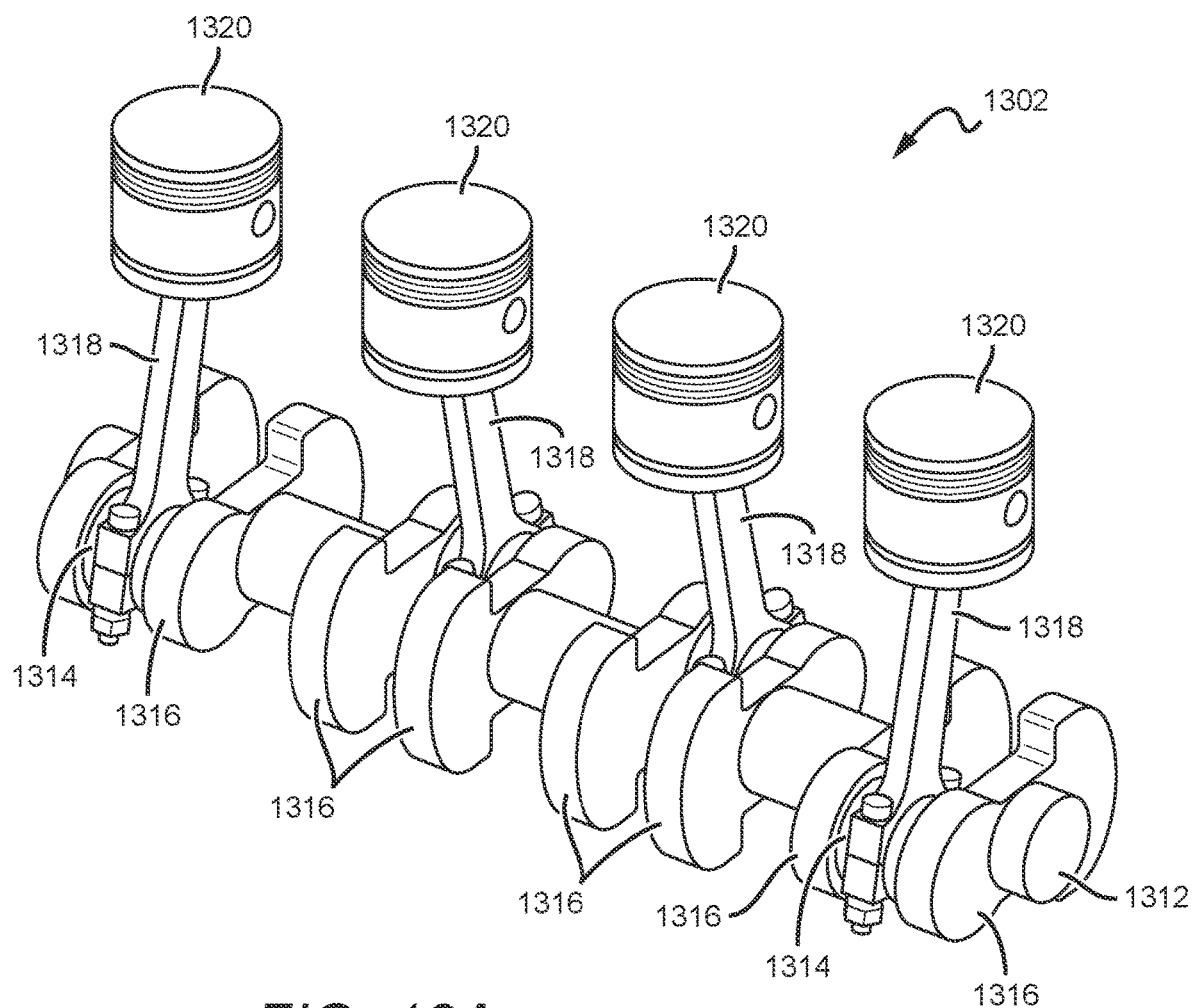
FIGS. 13A-13B illustrate another embodiment of a pump unit for an infusion pump.
Figure 13B:
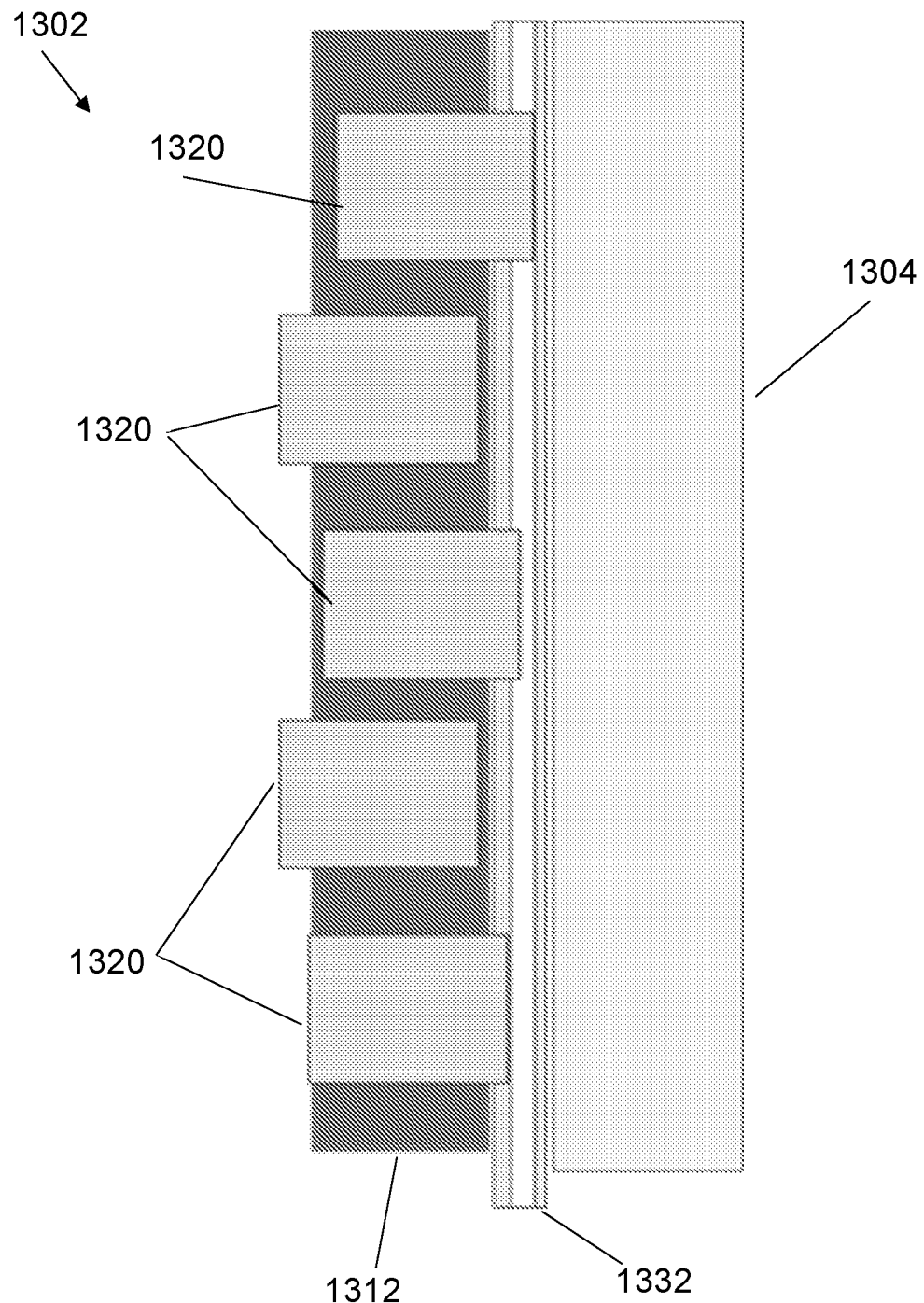

FIG. 13A-13B illustrate an alternative embodiment of a pump unit 1302 having a crank shaft 1312 to which pistons 1320 are attached via connecting rods 1318. As shown in FIG. 13A, the connecting rods 1318 are mounted eccentrically to an axle of the crank shaft 1312. Like the pump unit described above with respect to FIG. 10, the crank shaft 1312 can be driven by a variable-speed motor mechanically coupled to the crank shaft 1312 via one or more gears. In this manner, the motor can cause rotation of the crank shaft 1312 and control a speed of rotation of the crank shaft 1312.

Preferably, the crank shaft 1312 comprises a single injection molded piece to reduce overall wear of the crank shaft 1312 over time. The crank shaft 1312 preferably comprises a plurality of disks or sheaves 1316 disposed on an axle of the crank shaft 1312, with adjacent pairs of the disks or sheaves 1316 connected by a connecting bar 1314 that is disposed off-center of an axis of the crank shaft 1312. One end of each of the connecting rods 1318 is connected to one of the connecting bars 1314.

As the crank shaft 1312 rotates, the disks or sheaves 1316 also rotate which cause the connected pistons 1320 to move over time. It is contemplated that the pistons 1320 can be configured to contact the tubing 1332 of the cartridge 1330 as they move with respect to the axle of the crank shaft 1312 to thereby cause fluid to flow within the tubing 1332, such as shown in FIG. 13B. The pistons 1320 move in a specific manner with respect to the tubing 1332 to thereby force a flow of fluid within the tubing 1332. An increase in a rate of movement of the pistons 1320 will similarly increase a flow rate of the fluid within the tubing 1332. Similarly, a decrease in a rate of movement of the pistons 1320 will similarly decrease a flow rate of the fluid within the tubing 1332. With respect to the remaining numerals in FIGS. 13A-13B, the same considerations for like components with like numerals of FIG. 10 apply.

Figure 14A:
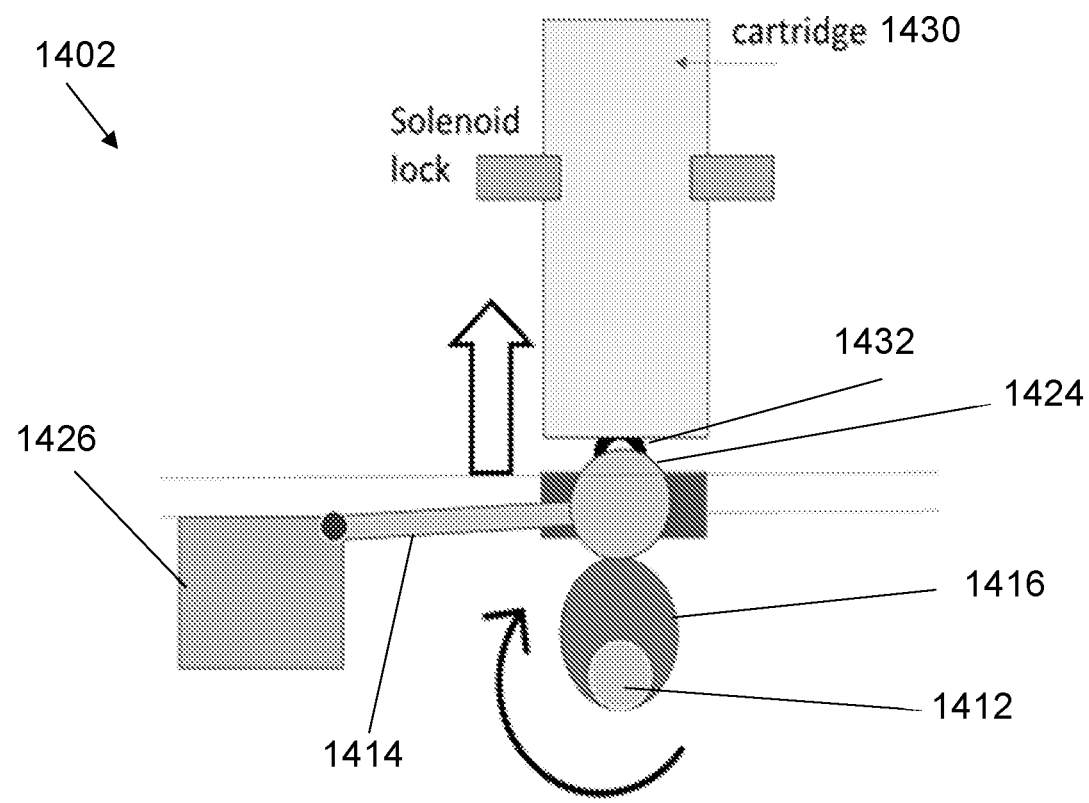
FIGS. 14A-14B illustrate another embodiment of a pump unit for an infusion pump.
Figure 14B:
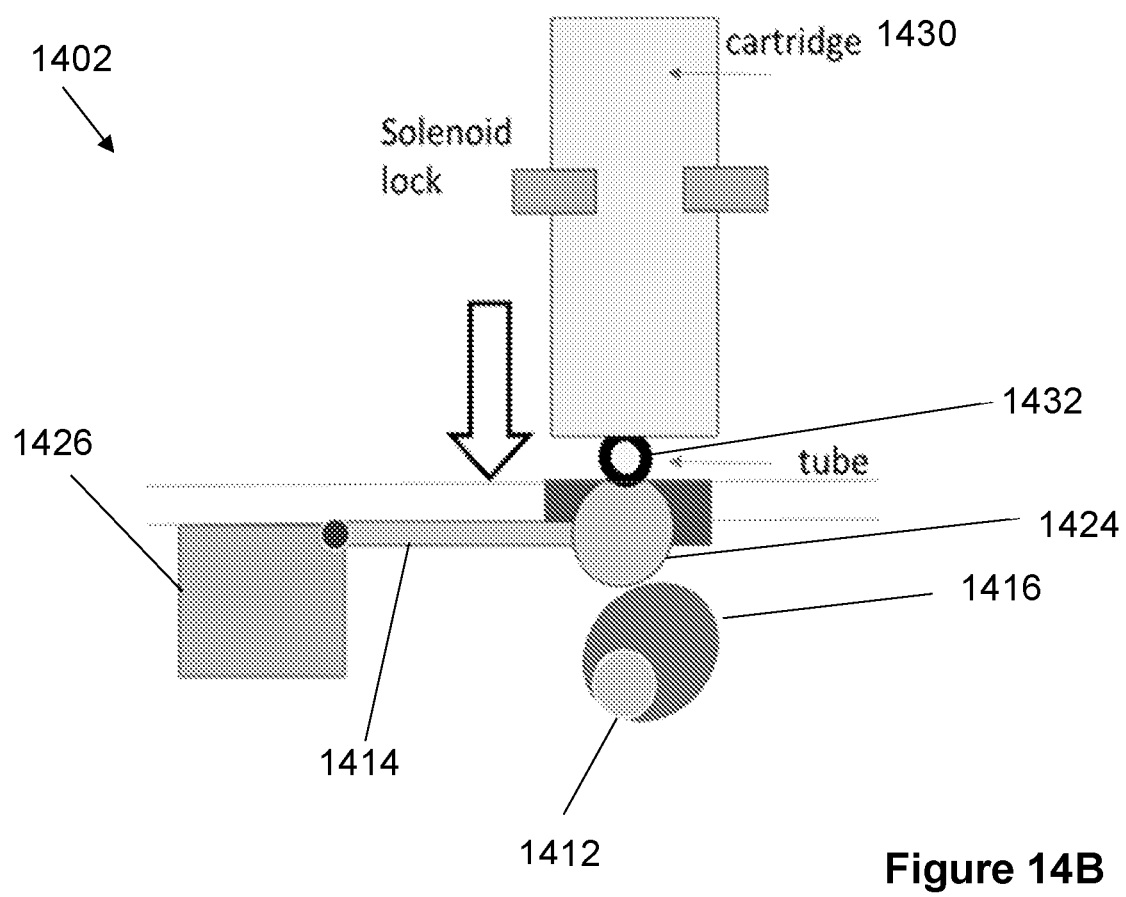

FIG. 14A-14B illustrate an alternative embodiment of a pump unit 1402 of an infusion pump having an eccentric cam 1412 comprising a plurality of circular disks or sheaves 1416 disposed on an axle of the cam 1412 such that a center of the disk or sheave 1416 is offset from a center of the axle of the cam 1412. Like the pump unit described above with respect to FIG. 10, the cam 1412 can be driven by a variable-speed motor mechanically coupled to the cam 1412 via one or more gears. In this manner, the motor causes rotation of the cam 1412.

Preferably, the cam 1412 comprises a single injection molded piece to reduce overall wear of the cam 1412 over time.

A plurality of intermediary pieces 1424 are disposed between the tubing 1432 of the cartridge 1430 and the disks or sheaves 1416, such that each intermediary piece 1424 is adjacent to one of the disks or sheaves 1416 and the tubing 1432. Each of the intermediary pieces 1424 can be pivotally coupled to a stationary piece 1426 via a connecting rod 1414. In this manner, as the cam 1412 rotates, each of the disks or sheaves 1416 will cause different ones of the intermediary pieces 1424 to press against the tubing 1432, such as shown in FIG. 14A, and then move away from the tubing 1432, such as shown in FIG. 14B. This generally sequential movement of the intermediary pieces 1424 against the tubing 1432 causes fluid to flow within the tubing at a rate corresponding to a rotation of the cam 1412.

Figure 15A:
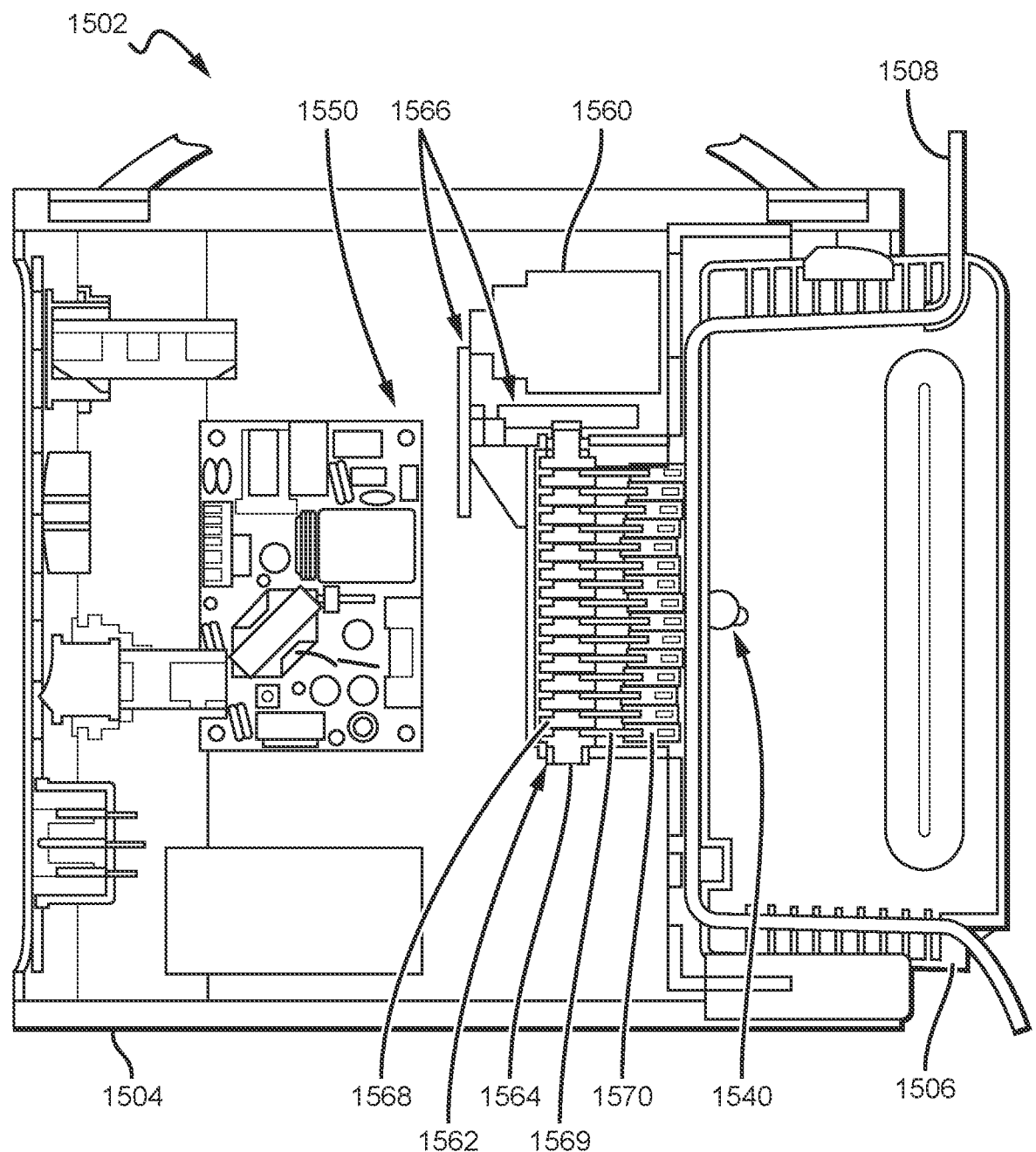
FIG. 15A illustrates a cross-section view of another embodiment of an infusion pump.
Figure 15B:
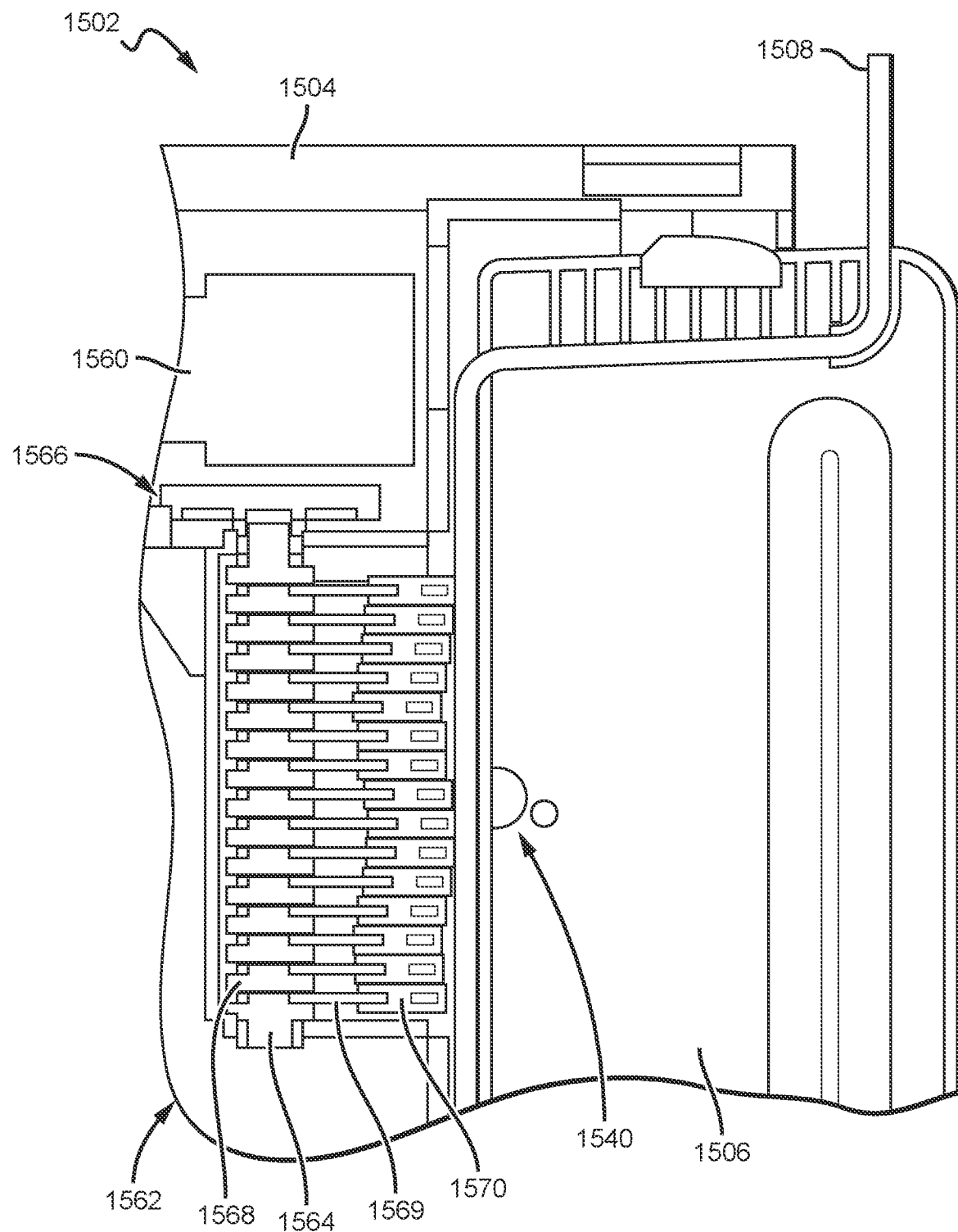
FIG. 15B illustrates an enlarged portion of the infusion pump of FIG. 15A.

FIGS. 15A-15B illustrates cross-sectional views of another embodiment of an infusion pump 1502 comprising a housing 1504 configured to receive a replaceable and/or disposable cartridge 1506 having a tubing 1508. As discussed above, when the cartridge 1506 is properly inserted into the infusion pump 1502, a portion of the tubing 1508 of the cartridge 1506 is disposed adjacent to a pump unit 1562. The tubing 1508 may extend through the cartridge 1506 to form a C-shape, for example.

The infusion pump 1502 preferably comprises a controller 1550 having a processor and memory, wherein the memory is configured to store one or more control algorithms. The controller 1550 is configured to control a motor 1560 of the pump unit 1562 which thereby regulates a flow of the fluid within the tubing 1508 of the cartridge 1506. In some embodiments, the controller 1550 can be configured to also control a latching mechanism 1540 such as one or more solenoids to release the cartridge 1506. The latching mechanisms 1540 can retain the cartridge 1506 within the housing 1504 of the infusion pump 1502 when engaged with the cartridge 1506. Preferably, the latching mechanisms 1540 comprise pull solenoids that engage with a notch or recessed area on left and right sides of the cartridge 1506, such as described above. In some embodiments, the cartridge 1506 comprises left and right indentations to facilitate a user's grip on the cartridge 1506.

Preferably, the motor 1560 comprises a variable-speed motor mechanically coupled to a crank shaft 1564 via a set of gears 1566. In this manner, the motor 1560 causes rotation of the crank shaft 1564 and control a speed of rotation of the crank shaft 1564. Preferably, the crank shaft 1564 comprises a single injection molded piece to reduce overall wear of the crank shaft 1564 over time. The crank shaft 1564 preferably comprises a plurality of circular disks or sheaves 1568 disposed on an axle of the crank shaft 1564. In some embodiments, at least some of the disks or sheaves 1568 are disposed on the axle such that a center of at least some of the disks or sheaves 1568 is offset from a center of the axle of the crank shaft 1564. It is contemplated that the crank shaft 1564 could be modular and replaceable, which allows the pump unit 1562 to be easily serviced over the lifespan of the pump unit 1562.

A set of pistons 1570 are each coupled to the crank shaft 1564 via a tie rod 1569. In preferred embodiments, the tie rods 1569 are mounted eccentrically to the axle of the crank shaft 1564. In some embodiments, the crank shaft 1564 the disks or sheaves 1568 are disposed on the axle of the crank shaft 1564, with adjacent pairs of the disks or sheaves 1568 connected by a connecting bar that is disposed off-center of the axis of the crank shaft 1564. One end of each of the tie rods 1569 is connected to one of the connecting bars, such as described above.

As the crank shaft 1564 rotates, the disks or sheaves 1568 also rotate which cause the connected pistons 1570 to move over time (compare position of pistons 1570 in FIG. 15A with FIG. 15B). It is contemplated that the pistons 1570 can be configured to contact the tubing 1508 of the cartridge 1506 as the pistons 1570 move back and forth with respect to the axle of the crank shaft 1564 to thereby cause fluid to flow within the tubing 1508 of the cartridge 1506. The pistons 1570 move in a specific manner with respect to the tubing 1508 to thereby force a flow of fluid within the tubing 1508. An increase in a rate of movement of the pistons 1570 will similarly increase a flow rate of the fluid within the tubing 1508. Similarly, a decrease in a rate of movement of the pistons 1570 will similarly decrease a flow rate of the fluid within the tubing 1508.

Figure 16A:
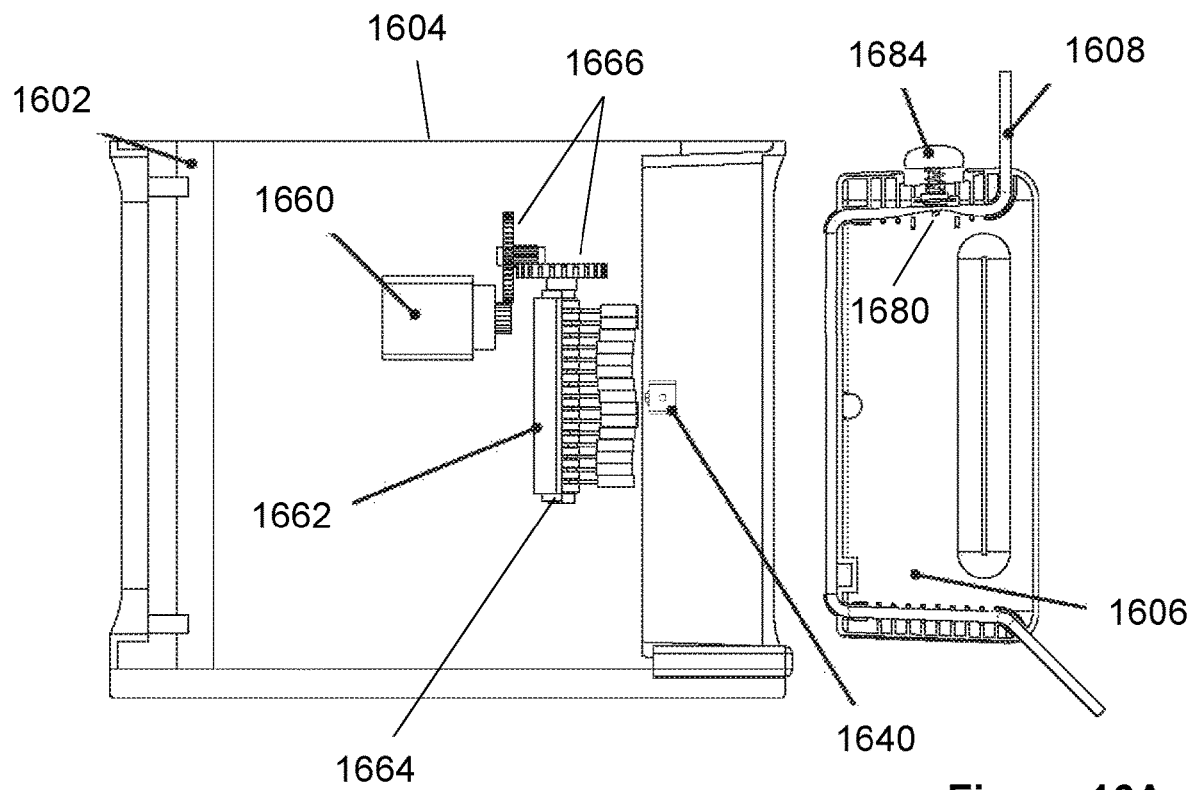
FIGS. 16A-16B illustrates a cross-section view of another embodiment of an infusion pump.
Figure 16B:
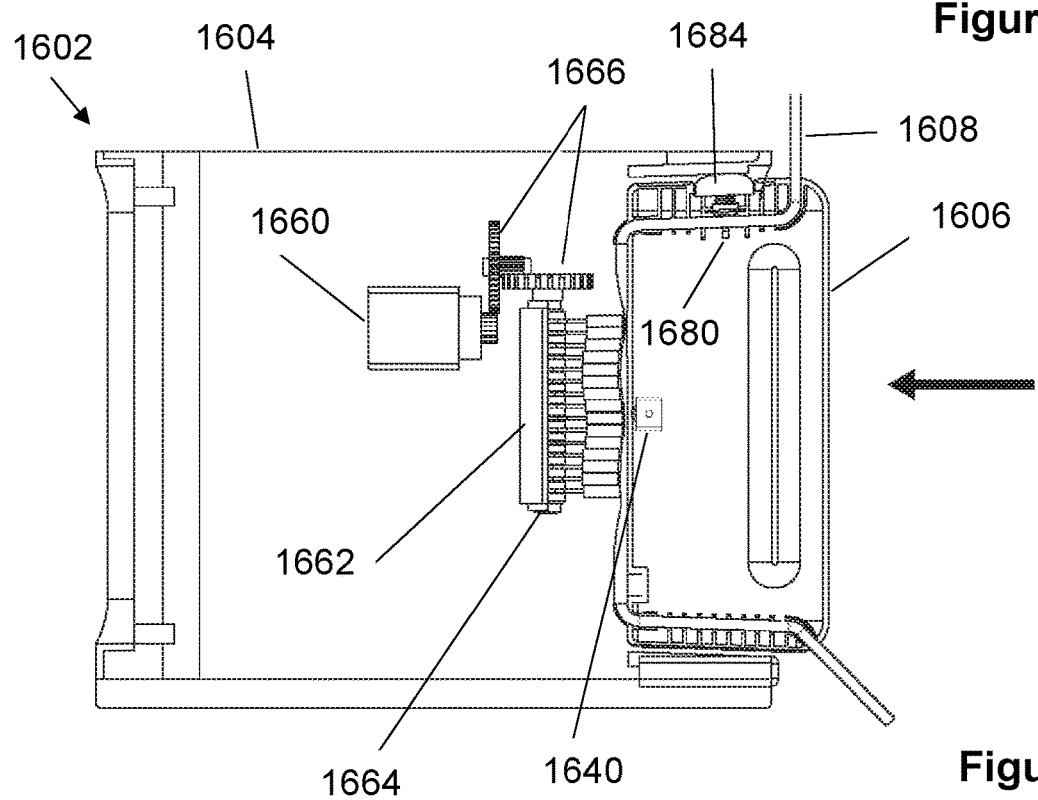

FIGS. 16A-16G illustrates cross-sectional views of another embodiment of an infusion pump 1602 comprising a housing 1604 configured to receive a replaceable and/or disposable cartridge 1606 having a tubing 1608. When the cartridge 1606 is properly inserted into the infusion pump 1602, as shown in FIG. 16B, a portion of the tubing 1608 of the cartridge 1606 is disposed adjacent to pistons 1670 of a pump unit 1662. The tubing 1608 may extend through the cartridge 1606 to form a C-shape, for example.

The infusion pump may also comprise one or more latching mechanisms 1640 that can be used to secure and release the cartridge 1606. For example, the latching mechanisms 1640 can retain the cartridge 1606 within the housing 1604 of the infusion pump 1602 when engaged with the cartridge 1606. Preferably, the latching mechanisms 1640 comprise pull solenoids that engage with a notch or recessed area on left and right sides of the cartridge 1606, such as described above. In some embodiments, the cartridge 1606 comprises left and right indentations to facilitate a user's grip on the cartridge 1606.

The infusion pump 1602 preferably comprises a motor 1660 configured to control a pump unit 1662 and thereby regulate a flow of the fluid within the tubing 1608 of the cartridge 1606. In some embodiments, a controller (such as shown in FIG. 15A) can be configured to control a speed of the motor 1660. Preferably, the motor 1660 comprises a variable-speed motor mechanically coupled to a crank shaft 1664 via a set of gears 1666.

FIG. 16C illustrates an enlarged portion of FIG. 16B, showing how the pistons 1670 interact with the tubing 1608 of the cartridge 1606. As can be seen, the motor causes rotation of the gears 1666, which in turn rotate the crank shaft 1664. As the crank shaft rotates, different ones of the pistons 1670 are pressed against the tubing 1608 causing the tubing 1608 to be compressed, while others of the pistons 1670 are moved away from the tubing 1608 and allowing the tubing 1608 to fill with fluid. The sequential nature of the movement of the pistons 1670 causes the fluid to move through the tubing 1608 in the direction shown in the Figure. An increase in a rate of movement of the pistons 1670 will similarly increase a flow rate of the fluid within the tubing 1608. Similarly, a decrease in a rate of movement of the pistons 1670 will similarly decrease a flow rate of the fluid within the tubing 1608.

FIG. 16D illustrates an exploded view of a piston 1670 and a tie rod 1669, while FIG. 16E illustrates an assembled view of that portion of the pump unit 1662. As shown, the piston 1670 is connected to a circular disk or sheave 1668 by the tie rod 1669, with one end of the tie rod 1669 having an aperture 1671 that is configured to receive a projection 1672 of the circular disk or sheave 1668.

As shown in FIG. 16C, the crank shaft 1664 preferably comprises a plurality of the circular disks or sheaves 1668 disposed in series along on an axle of the crank shaft 1664. In preferred embodiments, the tie rods 1669 are mounted eccentrically to the axle of the crank shaft 1664. For example, the projection 1672 of each sheave 1668 may be disposed off center from a center of the sheave 1668 and/or the sheave 1668 may be an ovular or other shape. It is contemplated that the sheaves 1668 are sized and shaped and/or disposed on the axle of the crank shaft 1664 in such a manner so that different ones of the pistons 1670 will press against the tubing 1608 at different times based on the relationship between the piston 1670, the sheave 1668 and the crank shaft 1664.

Figures 16F, 16G:
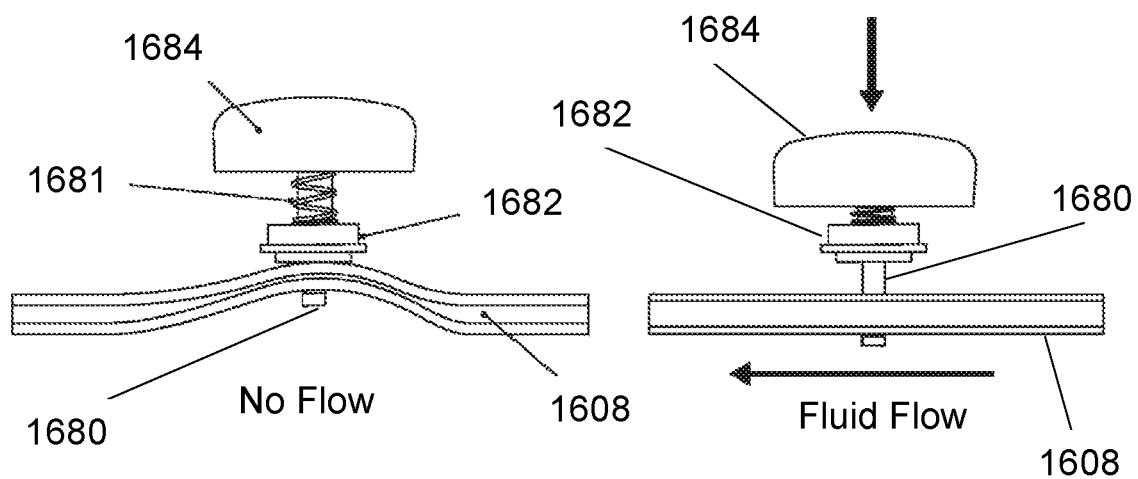
FIGS. 16F-16G illustrate side views of one embodiment of an actuator and valve of a cartridge.

In preferred embodiments, the cartridge 1606 comprises a valve 1680 that can be used to inhibit a flow of fluid within the tubing 1608 of the cartridge 1606. Preferably, the valve 1680 is biased in a closed position shown in FIG. 16A and FIG. 16F such as by use of a spring 1681 that causes the valve to compress a stopper 1682 against the tubing 1608. The valve preferably comprises the stopper 1682 and a hook that wraps around at least a portion of the tubing 1608. When the stopper 1682 and hook are moved closer together, this compresses the tubing 1608 preventing fluid from flowing through the compressed portion of the tubing 1608 as shown in FIG. 16F.

An actuator 1684 can be used to move the hook of the valve 1680 away from the stopper 1682 and thereby no longer compress the tubing 1608. Thus, when a force is applied to the actuator 1684, such as shown in FIG. 16G, the tubing 1608 is no longer compressed and fluid can flow through the tubing 1608.

Preferably, the actuator 1684 is disposed on, and extends outwardly away from, an outer surface of the cartridge 1606. Because the cartridge 1606 is sized to be held in one hand, the medical professional can hold the cartridge in one hand and prime the cartridge 1606 by depressing the actuator 1684 using a finger of that. As shown in FIG. 16B, the actuator 1684 can be depressed and remain in that position by a surface of the housing 1604 of the pump 1602 when the cartridge 1606 is inserted within the housing 1604.

The various embodiments described above can further including a spring or other mechanism positioned near the back of the cartridge near the pump unit that facilitates ejection of the cartridge from the infusion pump when the latching mechanism is released. Rather than, or in addition to, a spring, a push solenoid could be disposed within the housing and configured to contact the cartridge and facilitate ejection of the cartridge from the hollow interior portion when the push solenoid is actuated.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing measurements, quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A fluid delivery system, comprising:
 a pump unit disposed within the housing and comprising a motor mechanically coupled with a crank shaft having a set of sheaves disposed on or connected to the crank shaft;
 wherein the pump unit further comprises a set of pistons and a set of tie rods, and wherein each of the pistons is coupled to the crank shaft by one of the tie rods, such that the tie rod can move with respect to the piston, and wherein each of the tie rods are connected to one of the sheaves, such that the tie rod can move with respect to the sheave; and
 wherein the pistons are configured to move over time as the crank shaft rotates.

2. The fluid delivery system of claim 1, wherein the crank shaft and the set of sheaves comprise a single injection molded piece.

3. The fluid delivery system of claim 1, wherein the set of sheaves each comprises a projection that is configured to be received by one of the tie rods which connects the tie road to the sheave, and wherein the projection is disposed off center from an axle of the crank shaft and from a center of the sheave.

4. The fluid delivery system of claim 1, further comprising:
a controller having a processor and memory and configured to receive information and transmit command signals; and
wherein the controller is communicatively coupled to the pump unit and wherein the pump unit is configured to receive the command signals to thereby control a speed of the motor.

5. The fluid delivery system of claim 4, further comprising:
an infusion pump having a housing with a first opening and a hollow interior portion that is configured to receive a cartridge having the tubing, wherein when the cartridge is disposed within the hollow interior portion, the pistons are configured to compress different portions of the tubing of the cartridge over time as the crank shaft rotates;
a second infusion pump having a second housing with a second opening and a second hollow interior portion that is configured to receive a second cartridge having a second tubing;
a second pump unit disposed within the housing and comprising a second motor mechanically coupled with a second crank shaft having a second set of sheaves disposed on or connected to the second crank shaft; and
wherein the second pump unit further comprises a second set of pistons and a second set of tie rods, and wherein each of the pistons of the second set is coupled to the second crank shaft by one of the tie rods of the second set, and wherein each of the tie rods of the second set are connected to one of the sheaves of the second set;
wherein when the second cartridge is disposed within the second hollow interior portion, the pistons of the second set are configured to compress different portions of the second tubing of the second cartridge over time as the second crank shaft rotates; and
wherein the controller is communicatively coupled to the second pump unit and wherein the second pump unit is configured to receive the command signals.

6. The fluid delivery system of claim 1, further comprising:
at least one light source disposed within the housing and configured to illuminate the hollow interior and the cartridge.

7. The fluid delivery system of claim 1, further comprising:
a display communicatively coupled with an infusion pump comprising the pump unit, wherein the display can receive information from the infusion pump and transmit commands to the infusion pump to control the pump unit.

8. The fluid delivery system of claim 7, wherein the infusion pump further comprises a housing that comprises a slot configured to receive a portion of the display.

9. The fluid delivery system of claim 1, further comprising a sensor configured to monitor a flow rate of fluid within the tubing.

10. The fluid delivery system of claim 1, further comprising a sensor configured to determine properties of fluid within the tubing.

11. A cartridge for a fluid delivery system, comprising:
a housing comprising a top portion, a side portion, and a bottom portion, wherein the housing is configured to retain a portion of a tubing through which a medication can flow from a medication source to a patient, and wherein the tubing extends through the cartridge along the top portion, the side portion, and the bottom portion to form a C-shape, and wherein the tubing extends outside of the cartridge along at least one of the top portion, the side portion, and the bottom portion;
a valve configured to compress the tubing and prevent fluid flow in the tubing when the valve is in a first position; and
an actuator mechanically coupled to the valve, such that when a force is applied to the actuator, the valve is moved to a second position that allows fluid to flow through the tubing; and
wherein the valve is biased in the first position.

12. The cartridge of claim 11, wherein the valve comprises a hook and a stopper, and wherein the tubing is disposed between the stopper and the hook, and wherein the hook is configured to compress the tubing against the stopper and prevent fluid flow in the tubing when the valve is in the first position.

13. The cartridge of claim 11, wherein the housing comprises tapered top and bottom surfaces.

14. The cartridge of claim 11, wherein the housing is translucent.

15. The cartridge of claim 11, wherein the actuator is disposed on the top portion of the housing.

16. A fluid delivery system, comprising:
a cartridge comprising:
a cartridge housing comprising a top portion, a side portion, and a bottom portion, wherein the cartridge housing is configured to retain a portion of a tubing through which a medication can flow from a medication source to a patient, wherein the tubing extends through the cartridge along the side portion;
an infusion pump having a housing with a first opening and a hollow interior portion that is configured to receive the cartridge;
a pump unit disposed within the housing and comprising a motor mechanically coupled with a crank shaft having a set of sheaves disposed on or connected to the crank shaft;
wherein the pump unit further comprises a set of pistons and a set of tie rods, and wherein each of the pistons is coupled to the crank shaft by one of the tie rods, such that the tie rod can move with respect to the piston, and wherein each of the tie rods is coupled to one of the sheaves, such that the tie rod can move with respect to the sheave; and
wherein when the cartridge is disposed within the hollow interior portion, at least a portion of the tubing that extends along the side portion of the cartridge is compressed by one or more of the pistons over time as the crank shaft rotates.

* * * * *